(12) United States Patent
Eckert et al.

(10) Patent No.: US 6,313,373 B1
(45) Date of Patent: Nov. 6, 2001

(54) TISSUE SPECIFIC PROMOTERS AND TRANSGENIC MOUSE FOR THE SCREENING OF PHARMACEUTICALS

(75) Inventors: Richard L. Eckert, Cleveland Hts.; James F. Crish, North Olmsted, both of OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/430,201

(22) Filed: Oct. 29, 1999

Related U.S. Application Data
(60) Provisional application No. 60/106,495, filed on Oct. 30, 1998.

(51) Int. Cl.$^7$ .......................... G01N 33/00; C12N 15/00; C12N 5/00; A10K 67/00; C07H 21/02
(52) U.S. Cl. .................................. 800/18; 800/3; 800/25; 800/10; 435/320.1; 435/325; 435/455; 536/23.1
(58) Field of Search ........................ 536/23.1; 435/320.1, 435/325, 69.1; 800/3, 8, 21

(56) References Cited

U.S. PATENT DOCUMENTS

| | | |
|---|---|---|
| 4,683,195 | 7/1987 | Mullis et al. . |
| 4,683,202 | 7/1987 | Mullis . |
| 5,550,316 | 8/1996 | Mintz . |
| 5,578,444 | 11/1996 | Edwards et al. . |

OTHER PUBLICATIONS

Wall, 1996. Theriogenology, vol. 45, pp. 57–68.*
Mullins, et al., 1996. Journal of Clinical Investigation, vol. 98, No. 11, pp. S37–S40.*
Ebert, et al., 1988. Molecular Endocrinology, vol. 2, pp. 277–283.*
Bradley, et al., 1992. Biotechnology, vol. 10, pp. 534–539.*
Lopez–Bayghen, et al., 1996. Journal of Biological Chemistry, vol. 271, No. 1, pp. 512–520.*
Takahashi, et al., 1993. Dermatology, vol. 100, No. 1, pp. 10–15.*
Eckert, et al., 1986. Cell, vol. 46, pp. 583–589.*
Crish, et al., 1993. Differentiation, vol. 53, pp. 191–200.*
Crish, et al., 1998. Journal of Biological Chemistry, vol. 273, No. 46, pp. 30460–30465.*
Crish, et al., 1998, WO 98/42826, publication date Oct. 1, 1998.*
Griep et al. (1994) "Role of Papillornvirus Oncogenes in Human Cervical Cancer: Transgenic Animal Studies," Proc. Soc. Exp. Biol. Med. 206:24–34.
Kondoh et al. (1995) "Transgenic Models for Papillornavirus–Assciated Multistep Carcinogenis," Intervirology 38:181–186.
Yang et al., (1995) "The HPV 16 Genome Induces Carcinomas and T–Cell Lymphomas in Trangenic Mice," am. J. Pathol. 147:68–78.

Greenhalgh et al. (1994) "Transgenic Mice Expressing Targeted HPV–18 E6 and E7 Oncogenes in the Epidermis Develop Vernocous Leisons and Spontaneous, rad$^{Ha}$–activated Papillomas," Cell Growth Differ. 5:667–675.
Tinsley et al. (1992) "Abnormalities of epidermal differentation associated with expression of the human papillomarvirus type 1 early region in transgenic mice," J. Gen. Virol. 73:1251–1260.
Maniatis et al. (1987) "Regulation of Inducible and Tissue–Specific Gene Expression," Science 236:1237–1244.
Sambrook et al. (1989) *Molecular Cloning: A Laboratory Manual*, 2nd ed., Cold Spring Harbor Press, NY, pp. 16.7–16.8.
Sambrook et al. (1989) *Molecular Cloning: A Laboratory Manual*, 2nd ed., Cold Spring Harbor Press, NY, pp. 9.31–9.58.
Sambrook et al. (1989) *Molecular Cloning: A Laboratory Manual*, 2nd ed., Cold Spring Harbor Press, NY, pp. 7.39–7.52.
Eckert and Green "Structure and evolution of the human involucrin gene" Marcel Dekker (Ed.) NY, pp. 15–28.
Wheater et al. (1978) "Epithermal tissues," in *Fundamentals Histology*, 2nd Edition, Churchill Livingstone, NY, pp. 65–78.
Pitot (1978) "The Language of Oncology" in *Fundamentals of Oncology*, Marcel Dekker (Ed.), NY, pp. 15–28.
Green (1980) "The keratinocyte as differentiated cell type" The Harvey Lectures 74:101–139.
Eckert et al. (1997) "The epidermal keratinocyte as a model for the study of gene regulation and cell differentation" Physiol. Rev. 77:397–424.
Rice and Green (1979) "Presence in Human Epidermal Cells of a Soluble Protein Precursor of the Cross–linked Envelope: Activation of the Cross–Linking by Calcium Ions," Cell 18:681–694.

(List continued on next page.)

*Primary Examiner*—Deborah J. R. Clark
*Assistant Examiner*—Christopher Drabik
(74) *Attorney, Agent, or Firm*—Medlen & Carroll, LLP

(57) ABSTRACT

The present invention provides human involucrin (hINV) sequences having tissue specific and cell type specific promoter activity. The sequences provided herein direct expression to suprabasal cells of stratifying epithelia. The invention further provides methods for the production of transgenic animals which contain a hINV promoter sequence which directs the expression of human papillomavirus 16 oncogenes (or other oncogenes). These animals display cervical and epidermal hyperplasias as well as cancer of the trachea, esophagus, colon, epidermis, anus/rectum, lymph nodes, spleen and lung. The animals of the invention provide a useful model for screening potential anti-neoplastic compounds, carcinogens, and co-carcinogens for a number of cancers.

28 Claims, 15 Drawing Sheets

(5 of 15 Drawing Sheet(s) Filed in Color)

OTHER PUBLICATIONS

Thatcher and Rice(1985) "Keratinocyte–specific transglutaminase of cultered human epidermal cells: relation to cross–linked envelope formation and terminal differentation" Cell 40:685–695.
Kim et al. (1995) "Highly active soluble processed forms of the transglutaminase 1 enzyme in epidermal keratinocytes"J. Biol. Chem. 270:18026–18035.
Steinart (1995) Cell Death Differ. 2:33–40.
Murphy et al. (1984) "Involucrin expression in normal and neoplastc human skin: a marker for keratinocytes differentiation" J. Invest. Dermatol. 82:453–457.
Murphy et al. (1993) "A Dial Role for Involucrin in the Epidermis –Ultrasound Localization in Epidermis and Hair Follicle in Humans and Transgenic Mice," J. Struct. Biol. 111:68–76.
Stein and Marekov (1997) "Direct evidence that involucrin is a major early isopeptide cross–linked components of the keratinocyte cornified cell envelope" J. Biol. Chem. 272:2021–2030.
Rice and Green (1997) "The cornified envelope of terminally differentiated human epidermal keratinocyles consists of cross–linked protein" Cell 11:417–422.
Welter et al. (1995) "Fos–related Antigen (Fra–1), junB, and junD Activate Human Involucrin Promoter Transcription by Binding to Proximal and Distal API Sites to Mediate Phorbol Ester on Promoter Activity," J. Biol. Chem. 270:12614–12622.
Banks et al. (1999) "Transcription factor Sp1 activates involucrin promoter activity in non–epithelial cell types" Biochem. J. 337:507–512.
Carroll et al. (1993) "Tissue–and stratum–specific expression of the human promoter in transgenic mice,"Proc. Natl. Acad. Sci. USA 90:10270–10274.
Bickenbach et al. (1995) "Loricrin expression is coordinated with other epidermal proteins and the appearance of lipid lamellar granules in development" J. Invest. Dermatol. 104:405–410.
Dale et al. (1985) "Expression gene epidermal keratins and filaggrin during human fetal skin development"J. Cell Biol. 101:1257–1269.
Byrne et al. (1994) "Progamming gene expression in developing epidermis" Development 120:2369–2383.
Warbol et al., (1985) "Immuno–ultrastructural localization of involucrin in squamous epithelium and cultured keratinocytes"J. Histochem. Cytioche. 33:141–149.
Mehrel et al. (1990) "Indentification of a major keratinocyte cell envelope protein, locrin"Cell 61:1103–1112.
DiSepio et al. (1995) "The proximal promoter of the mouse loricrin gene contains a functional AP–1 element and directs keratinocyte–specific but not differentiation–specific expression" J. Bioll. Chem. 270:10792–10799.
Eckert et al. (1997) "The epidermis: genes on –genes off" J. Invest. Dermatol. 109:501–509.
Banks et al. (1998) "Characterization of human involucrin promoter distal regulatory region transcriptional activator elements–a role for Sp1 and AP1 binding sites"Biochem. J. 331:61–68.
Welter et al. (1996) "Regulation of Human Involucrin Promoter Activity by POU Domains Proteins," J. Biol. Chem. 271:14727–14733.
LaPres and Hudson (1996) "Identification of a functional determinant of differentiation–dependent expression in the involucrin gene" J. Biol. Chem. 271:23154–23160.

Efimova et al. (1998) "Regulation of human involucrin promoter activity by a protein kinase C, Ras, MEKKIm MEK3, p38/RK, AP1 signal transduction pathway" J. Biol. Chem. 272:24387–24395.
Caruthers et al. (1980) "New chemical methods for synthesizing polynucleotides," Nuc. Acids Res. Symp. Ser. 215–223.
Horn et al. (1980) "Synthesis of oligonucleotides on cellulose. Part II: design and synethic strategy to the synethsis of 22 oligodeoxynucleotides coding for Gastric Polypeptide (GIP)[11]," Nuc. Acids Res. Symp. Ser. 225–232.
Barany (1991) "Genetic disease detection and DNA amplification using cloned thermostable ligase," Proc. Natl. Acad. Sci. 88:189–193.
Barany (1991) "The Ligase Chain Reaction in A PCR World," PCR Methods and Applic. 1:5–16.
Wu and Wallace (1989) "The Ligation Amplification Reaction (LAR) –Amplification of Specific DNA Sequences Using Sequential Rounds of Temple–Dependent Ligation," Genomics 4:560–569.
Kistner et al. (1996) "Doxycycline–mediated quantitative and tissue–specific control of gene expression in transgenic mice," Proc. Natl. Acad. Sci. USA 93:10933–10938.
Barlett et al. (1996) "Efficient expression of protein coding genes from the murine U1 small nuclear RNA promoters," Proc. Natl. Acad. Sci. USA 93:8852–8857.
Wigler et al. (1977) "Transfer of Purified Herpes Virus Thymidine Kinase Gene to Cultured Mouse Cells,"Cell 11:223–232.
Lowy et al. (1980) "Isolation of Transforming DNA: Cloning the Hamster aprt Gene,"Cell 22:817–823.
Wigler et al. (1980) "Transformation of mammalian cells with an amplifable dominant–acting gene,"J. Mol. Biol. 150:1–14.
Hartman and Mulligan (1988) "Two dominant–acting selectable markers for gene transfer studies in mammalian cells," Proc. Natl. Acad. Sci. 85:8047–8051.
Rhodes et al. (1995) "Transformation of Maize by Electroporation of Embryos," Methods in Mol. Biol. 55:121–131.
Gall and Pardue (1981) "Nucleic Acid Hybridization in Cytological Preparations," Meth. Enzymol. 21:470–480.
Angerer et al. (1985) "In Situ Hybridazation to Cellular RNAs", in Genetic Engineering: *Principles and Methods*. vol. 7, pp. 43–65, Setlow & Hollander (Eds). Plenum Press, NY.
Maddox et al. (1983) "Elevated Serum Levels in Human Pregnancy of a Molecule Immunochemically Similar to Eosinophil Granule Major Basic Protein," J. Exp. Med. 158:1211–1226.
Palmier (1986) "Gerin–Line Transformation of Mice," Ann. Rev. Genet. 20:465–499.
Brinster et al. (1985) "Factors affecting the efficiency of introducing foreign DNA into mice by microinjecting eggs, "Proc. Natl. Acad. Sci. USA 82:4438–4442.
Gordon and Ruddle (1983) "Gene Transfer into Mouse Embryos: Production of Trangenic Mice by Pronuclear Injection," Meth. Enzymol. 101:411–433.
Hammer et al. (1986) "Genetic Engineering of Mammalian Embryos," J. Animal Sci. 63:269–278.
Hammer et al. (1985) "Production of transgenic rabbits, sheep and pigs by microinjection," Nature 315;680–683.
Wagner et al. (1984). *Theriogenology*21–29.

Jaenisch (1976) "Germ line integration and Mendelian transmission of the exogenous Moloney leukemia virus,"Proc. Natl. Acad. Sci. USA 82:6927–6931.

Jahner et al. (1985) "Insertion of the bacterial gpt gene into the germ line of mice by retroviral infection," Proc. Natl. Acad. Sci. USA 82:6927–6931.

Van der Putten et al. (1985) "Efficient insertion of genes into mouse germ line via retroviral vectors," Proc. Natl. Acad Sci USA 82:6148–6152.

Stewart et al. (1987) "Expression of retroviral vectors in transgenic mice obtained by embryo infection," EMBO 6:383–388.

Jahner et al. (1982) "*De novo*methylation and expression of retroviral genomes during mouse embrogenesis," Nature 298:623–628.

Evans and Kaufman (1981) "Established in culture of pluripotential cells from the mouse embryos," Nature 292:154–156.

Martin (1981) "Isolation of a pluripotents cell line early mouse embryos cultured in medium conditioned by teratocarcinoma stem cells," Proc. Natl. Acad Sci. USA 78:7634–7638.

Magnuson et al. (1982) "The Development of monosomy 19 mouse embryos," J. Embryos. Exp. Morph. 69:223–236.

Doetschman et al. (1988) "Establishment of the Mouse Embryonic Stem Cell Lines from Whole Blastocyles and Isolates Inner Cell Masses," Jpn. J. Anim. Reprod. 35:113–178.

Tokunaga et al. (1989) "Establishment of the Mouse Embryonic Stem Cell Lines from Whole Blastocysts and Isolated Inner Cell Masses," Jpn. J. Anim. Reprod. 35:113–178.

Eistetter (1989) "Pluipotent Embroynal Stem Cell Lines Can Be Established from Disaggerated Mouse Morulae," Dev. Gro. Differ. 31:275–282.

Matsui et al. (1992) "Derivation of Pluripotential Embryonic Stem Cells from Murine Primordial Germ Cells in Culture," Cell 70:841–847.

Resnick et al. (1992) "Long–term proliferation of mouse primordial germ cells in culture," Nature 359:550–551.

Johnson et al. (1989) "Genetic Correction of Heredity Disease," Fetal Ther. 4 (Suppl. 1):28–39.

Bradley et al. (1984) "Formation of germ–line chimaeras from embryo–derived teratocarcinoma cell lines," Nature 309:255–256.

Bradley (1987) "Production and analysis of chimaeric mice," in *Teratocarcinomas and Embryonic Stem Cells: A Pratical Approach*, E. J. Robertson, ed, IRL Press, Oxford, UK, pp. 113–151.

Nagy et al. (1990) "Embryonic stem cells alone are able to support fetal development in the mosue," Development 110:815–821.

Eckert (1987) "New vectors for rapid sequencing of DNA fragments by chemical degradation"Gene (Amst.) 51:247–254.

Sanger et al. (1977) "DNA sequencing with chain–terminating inhibitors" Proc. natl. Acad. Sci. USA 74:5463–5467.

LaCelle et al. (1998) "In vitro cross–linking of recombinant human involucrin" Pharmacol Appl Skin Physiol 11:214–226.

Banks–Schlegel et al. (1981) "Involucrin synthesis and tissue assembly by keratinocyles in natural and cultured human epithelia" J. Cell Biol. 90:732–737.

Louden et al. (1993) "Species Difference in Binding of Submandibular Nuclear Proteins to Renin DNA," Clin. Exp. Pharm. Phys. 20:283–288.

Strojek et al. (1988) "The Use of Tragenic Animal Techniques for Liverstock Improvement," In *Genetic Engineering: Principles and methods*, vol. 10, pp. 221 and 238.

Hammer et al. (1990) "Spontaneous Inflammatory Disease in Transenic Rats Expressing HLA–B27 and Human $\beta_2$m: An Animal Model of HLA–B27–Associated Human Disorders," Cell 63:1099–1112.

Lewin (1985) Genes II, pp. 76–79.

Association of Biomolecular Resource Facilities (www.abrf.org), accessed Apr. 3, 2000.

* cited by examiner

```
                                                                HindIII                              AP1-5/Sp1                    HaeII                                                                                      AccI -2473 AAGCTT CTCCATG
       TGTCATGGATATAGCTCATCCTTATTATGTTGGGTGTGGGGTTGGACAGTTACCCAGACT
-2460  TGTCATGTGGACCTGGAGCTTATGAGGTCATTCACATAGGCAGTGAAAGAACCTCTCCCA
-2340  TATACGTGAATGCCTGTCTCCCAAATGGGCAACCTGTGGGCAGAATAAGGGACTTCTCA
-2220  GCCCTAGAATGTTGAGGTTTCCCCAACCTCCCTTGCATACACACACACACAAACACTC
       CCTCAGCTGTATCCACTGCCCTCTTTCCCACACCCTAGCTTTGCCCAGCAGTCAAAGGCT
-2100  CACACATACCATCTTCTCCTTAAGGCTCTTATTATGCCGTGAGTCAGAGGGCGGAGGCA
       GATCTGGCAGATACTGAGCCCTGCTAACCCATAAGACCGGTGTGACTTCCTTGATCTGA
       GTCTGCTGCCCCAGACTGACTGTCACGGCTGGGAGAGGCAGATTCCCCCAGATGAAG
-1980  TCAGCAGCAGACAGAGCACAAGGGCATC AGCGCC AAAGTAAGGATGCTTGATTAGTTCTTCAGG
       GCAGAGTGGGCTGTGCTTCCTGCCCCAGAAAATGGCACAGTCCCTGTTCTATGAGGAAA
-1860  AAGAATGTGAGGTCCCTGGGCTCAGGGAACAGAGAGGTCATGAGGAGGGATAGCA
       CTGCAGAAACCAAGGTGCCTTGTGAGTCCTCCCTCGTCTCTTTTTAGCATGATCCAGA
-1740  ACATGACAAAATTAGTGTCTTTAAATAGATTTACTTGGCTAAGACAAATGTGCCTGTCAG
       GAAAACTATGGGAATCAGACACTTCTCAAAATTAGCCCCACTGAGTATTGTCTTTATA
-1620  ATTCCTTCTTTTGGATTAGATTGTAAAAAGAGAAGAGTGTAAATAAATGATGTCCATATAA
       TAAGTTATTAGCCAACCATTAAATCAGACATATAAACATTGATCAACACTGAAATGTTTAATAGTCATTAT
-1500  ACACATACAGACAAACACACACATAAATTCACTGTTCTTCAATGAATACTTGTAGAGCACATATTATATGCA
       TTTCGGTCGTAAAATTCACTGTCTTCTAGGGTATAGTGAAAACATACCAG GTATAC GCTGCTCTTAG
-1380  GTAGTTTTGATAGGTTCTAGGGAAAGATAAGACAATAAGCAAGTGAACAAATGCAAATAAATTACTC
       CTTATTTCCAGTGGGAAAGATAGAACAATAAGACAAGTGAACAAATGCAAATAAATTACTC
-1260  TAGATTGTTATAAGTGAAATTAAGTACACTGACATCCTTTAGATATATGGTACACAGAGAAGGATC
       TCTGACAGACCCCAACATTGACACTGAAGCTCATAAAGAACCAGAGAGACCTGGG
-1140  GAGGGCCGGTGGGCAGAAGGAGGAGCAGGTGCCAAGCCCCAGGTGGAGAGCTCTGGGCT
       CATCTCAGGAACCGAAGGCCCCTGAGGTAAGAATATACCTCTCAGGAGGAGATTGAC
```

FIG. 6

```
                                          KpnI
-1020  ATGAATTGGGGCCCCAGAAGAAGGCAGAAGCCAGGTACCCAGGGTCTCTTTAAACCACGGC
       AGTGAGTTTGAATGTTATTTCAAGTGTGTCTGTGGTGGCACGGGGAGAGATGTG
 -900  CTCAAATCCCCACTCTGAAAGATTTCTTAAGCTATTTCTAGAGTATGATTTACAACAGGA
       AATGGATGATTTGATTCTGATCTTTATGCCTTCATTTAAAAAGTACTTAAGAAAG
 -780  TAGTTTGGTTTGTCATTATAAAAGCAATACTTATTTTATATTGTGTAGATTCAATCTT
       GTTTCCTTGCCTAGAGTGGGGCCGTGCTTTGGAGTTCTTATGAGCATTGCTGAGAA
                                                                      AP1-4
 -660  CTTCTCTAACTGCAGCCCTCGGGCATAGAGGCTGGGCAGCAGTGGCAGCAGAGGACT         AP1-3
       CCTAGAAGCCTTCTCTACTTGACTCTGGCCTAAAGTCAAACTCCCCACCAAAGACA
 -540  GAGTTTATTTCCACATAGGATGGAGTTAAAAAATATATTCTGAGAGGAAGGGCTGTG         AP1-2
       GCCCAAGAGAACACCCCAGAATACCACCCCCTTCATGGAAGTGACTCTATCTTCAAACA     AP1-1
 -420  TATAACCCAGCCCTGGACATCCCCGAAAGACACATAACTTTCCATTTCATGCCCTTGAAAG     CeIII
       TGAATCTTTTGGCTAAGGTCACTAAGGAGAACAAACTCATTTTGAAAGTGAAAAATTGAGATTC
 -300  AGAGCAGAAGTTTGACTAAGGTCACAGAGAATCACACAGAGTTGAGCTACCAGAATCCTCTGGCCAGGAG
       TAGGTCAGAAAAGCATCACAGGAATGGGGCCCTAAAGGGTTTGCTGCTTAAGATGCCTGTGGTGAG
 -180  CTGTGTGTCCCTGGGAAATGGGGCCCTAAAGGGTTTGCTGCTTAAGATGCCTGTGGTGAG
       TCAGGAAGGGGTTAGAGGAAGTTGACCAACTAGAGTGGTGAAACCTGTCCATCACCTTCA
  -60  ACCTGGAGGGAGGCCAGGCTGCAGAATGATATAAAGAGTGCCCTGACTCCTGCTCAGCTC
                                                             -1
```

FIG. 6 cont.

5'-GCCGTGAGTCAGAGGGCGGGAGGC-3'  AP1-5/Sp1
5'-GCCG<u>AGCTC</u>CAGAGGGCGGGAGGC-3'  AP1-5mm/Sp1

A Esophagus
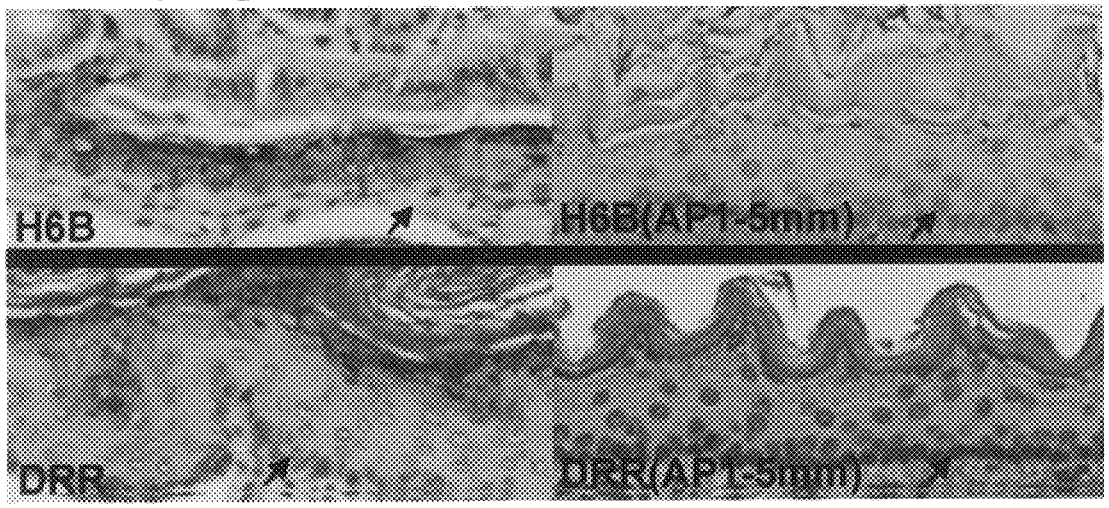
B Cervix
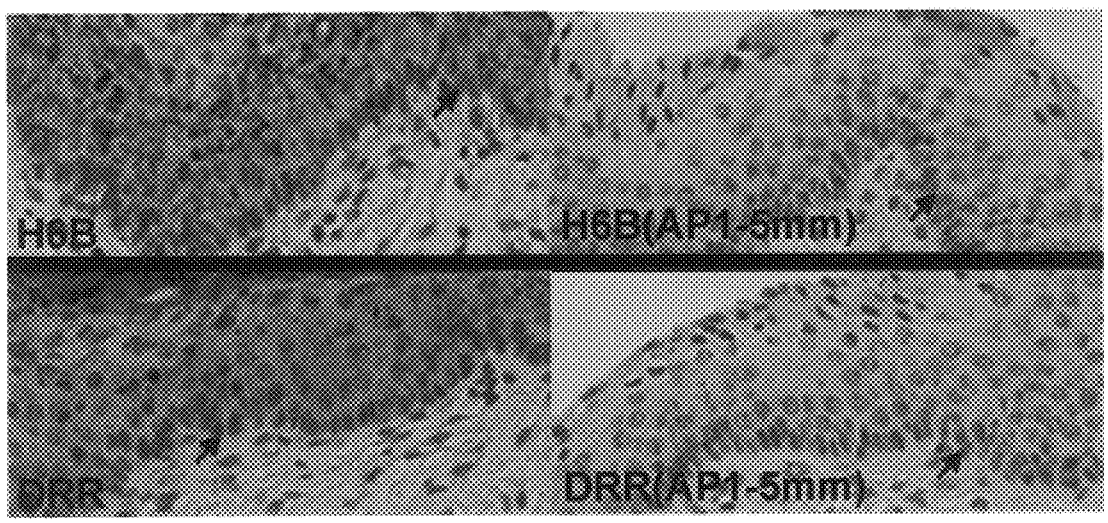
FIG. 11

```
ORIGIN
    1 ttaaatagtt ctatgtcagc aactatagtt taaacttgta cgtttcctgc ttgccatgcg
   61 tgccaaacta caataattca tgtataaaac taagggcgta accgaaatcg gttgaaccga
  121 aaccggttag tataaaagca gacattttat gcaccaaaag agaactgcaa tgtttcagga
  181 cccacaggag cgacccagaa agttaccaca gttatgcaca gagctgcaaa caaccataca
  241 tgatataata ttagaatgtg tgtactgcaa gcaacagtta ctgcgacgtg aggtatatga
  301 ctttgctttt cgggatttat gcatagtata tagagatggg aatccatatg ctgtatgtga
  361 taaatgttta aagtttattt ctaaaattag tgagtataga cattattgtt atagtgtgta
  421 tggaacaaca ttagaacagc aatacaacaa accgttgtgt gatttgttaa ttaggtgtat
  481 taactgtcaa aagccactgt gtcctgaaga aaagcaaaga catctggaca aaaagcaaag
  541 attccataat ataagggggtc ggtggaccgg tcgatgtatg tcttgttgca gatcatcaag
  601 aacacgtaga gaaacccagc tgtaatcatg catggagata cacctacatt gcatgaatat
  661 atgttagatt tgcaaccaga gacaactgat ctctactgtt atgagcaatt aaatgacagc
  721 tcagaggagg aggatgaaat agatggtcca gctggacaag cagaaccgga cagagcccat
  781 tacaatattg taaccttttg ttgcaagtgt gactctacgc ttcggttgtg cgtacaaagc
  841 acacgtag acattcgtac tttggaagac ctgttaatgg gcacactagg aattgtgtgc
  901 cccatctgtt ctcagaaacc a
```

FIG. 13

SEQUENCE LISTING

<160> NUMBER OF SEQ ID NOS: 8

<210> SEQ ID NO 1
<211> LENGTH: 2473
<212> TYPE: DNA
<213> ORGANISM: Homo sapiens

<400> SEQUENCE: 1

```
aagcttctcc atgtgtcatg ggatatagct catccttatt atgttgggtg ggggttggac      60
agttacccag acttgtcatg tggacctgga gcttatgagg tcattcacat aggcagtgaa     120
agaacctctc ccatatacgt gaatgcctgt ctcccaaatg gggcaacctg tgggcagaat     180
aagggacttc tcagccctag aatgttgagg tttccccaac ccctcccttg catacacaca     240
cacacaaaca ctccctcagc tgtatccact gccctctttc ccacaccta gctttgccca      300
gcagtcaaag gctcacacat accatcttct ccttaaggct cttattatgc cgtgagtcag     360
agggcgggag gcagatctgg cagatactga gccctgcta acccataaga ccggtgtgac      420
ttccttgatc tgagtctgct gccccagact gactgtcacg ggctgggaag aggcagattc     480
cccccagatg aagtcagcag cagagcacaa gggcatcagc gccaaagtaa ggatgcttga     540
ttagttcttc agggcagagt gggctgtgct tcctctgccc cagaaaatgg cacagtccct     600
gttctatggg aaaaagaatg tgaggtccct gggtgggctc agggaacaga gaggtcatga     660
ggagggata gcactgcaga aaccaagggt gccttgtgag tcctccctct gtcttttag       720
gcatgatcca ggaacatgac aaaattagtg ctttaaatag atttacttgg gctaagagaa     780
atgtgcctgt caggaaaact atggggaatc aggacacttc tcaaaattag ccccactgag     840
tattgtcttt ataattcctt ctttttggat tagattgtaa aaaagagagt gtaaatgaat     900
gatgtccata taataagtta ttagccaacc attaaaaaga aagggaagaa ataaatcagt     960
ttggttttta cacacacata cagacacaca catataaaca ttgatcaaca ctgaaatgtt    1020
taatagtcat tatttcggg tcgtaaaatt cactgttctt caatgaatac ttgtagagca     1080
catattatat gcagtagttt tgataggttc taggggtata gtggaaaaca taccaggtat    1140
acgctgctct tagcttattt tccagtggga aagatagaca ataagcaagt gaacaaatgc    1200
aaataaatta ctctagattg ttataagtga aattaagtac caatccttta gatatggtac    1260
acagagaagg atctctgaca gaccccaaca ttgacactga agctgaaagg cataaaagaa    1320
ccagagacct ggggaggggc cggtgggcag aaggagagca ggtgccaagc ccccaggtgg    1380
agagctctgg gctcatctca ggaaccgaag gccctcagtg aggtaagaat atacctctca    1440
gggagagatt gacatgaatt ggggcccag aagaaggcag aagccaggta cccagggtct     1500
tttaaaccac ggcagtgagt ttgaatgtta tttcaagtgt gctggtgcac tgttggcacg    1560
ggggagagat gtgctcaaat ccccactctg aaagatttct taagctattt ctagagtatg    1620
atttacaaca ggaaatggat gatttgattc tgatctttat gccttcatgc atttaaaaaa    1680
```

```
gtacttaaga aagtagtttg gtttgtcatt ataaaaagca atacttattt ttatattgtg    1740
tagattcaat cttgtttcct tgcctagagt gggccgtgct ttggagttct tatgagcatg    1800
gcattcctga gaacttctct aactgcagcc tcgggcatag aggctgggca gcaagtggca    1860
gcagcagagg actcctagaa gccttctact tgactctact tggcctaaag tcaaactccc    1920
tccaccaaag acagagttta tttccacata ggatggagtt aaaaaatata ttctgagaga    1980
ggaagggctt gtggcccaag agaacacccc agaaatacca cccttcatg ggaagtgact      2040 ctatcttcaa acatataacc cagcctggac atccccgaaa gacacataac tttccatttc    2100
atgcccttga aagtgaatct tttggcctaa taatgagaac aaactcattt tgaaagtgga    2160
aaaattgaga ttcagagcag aagtttgact aaggtcacaa acagtagga tgcctcactc      2220 agctccctgt gcctaggtca gaaaagcatc acaggaatag ttgagctacc agaatcctct    2280
ggccaggcag gagctgtgtg tccctgggaa atggggccct aaagggtttg ctgcttaaga    2340
tgcctgtggt gagtcaggaa ggggttagag gaagttgacc aactagagtg gtgaaacctg    2400
tccatcacct tcaacctgga gggaggccag gctgcagaat gatataaaga gtgccctgac    2460
tcctgctcag ctc                                                      2473

<210> SEQ ID NO 2
<211> LENGTH: 18
<212> TYPE: DNA
<213> ORGANISM: Homo sapiens

<400> SEQUENCE: 2
ctccaccaaa gcctctgc                                                   18

<210> SEQ ID NO 3
<211> LENGTH: 18
<212> TYPE: DNA
<213> ORGANISM: Homo sapiens

<400> SEQUENCE: 3
ctgcttaagc tgctgctc                                                   18

<210> SEQ ID NO 4
<211> LENGTH: 8
<212> TYPE: DNA
<213> ORGANISM: Homo sapiens

<400> SEQUENCE: 4 tgagtcag                                                               8

<210> SEQ ID NO 5
<211> LENGTH: 7
<212> TYPE: DNA
<213> ORGANISM: Homo sapiens

<400> SEQUENCE: 5 gggcggg                                                                7

<210> SEQ ID NO 6
<211> LENGTH: 456
<212> TYPE: DNA
<213> ORGANISM: Homo sapiens

<400> SEQUENCE: 6
atgtttcagg acccacagga gcgacccaga aagttaccac agttatgcac agagctgcaa     60
acaaccatac atgatataat attagaatgt gtgtactgca agcaacagtt actgcgacgt    120
```

```
                                               -continued gaggtatatg actttgcttt tcgggattta tgcatagtat atagagatgg gaatccatat       180
gctgtatgtg ataaatgttt aaagttttat tctaaaatta gtgagtatag acattattgt       240
tatagtgtgt atggaacaac attagaacag caatacaaca aaccgttgtg tgatttgtta       300
attaggtgta ttaactgtca aaagccactg tgtcctgaag aaaagcaaag acatctggac       360
aaaaagcaaa gattccataa tataagtggg cggtggaccg gtcgatgtat gtcttgttgc       420
agatcatcaa gaacacgtag agaaacccag ctgtaa                                 456

<210> SEQ ID NO 7
<211> LENGTH: 294
<212> TYPE: DNA
<213> ORGANISM: Homo sapiens

<400> SEQUENCE: 7
atgcatggag atacacctac attgcatgaa tatatgttag atttgcaacc agagacaact        60
gatctctact gttatgagca attaaatgac agctcagagg aggaggatga aatagatggt       120
ccagctggac aagcagaacc ggacagagcc cattacaata ttgtaacctt ttgttgcaag       180
tgtgactcta cgcttcggtt gtgcgtacaa agcacacacg tagacattcg tactttggaa       240
gacctgttaa tgggcacact aggaattgtg tgccccatct gttctcagaa acca            294

<210> SEQ ID NO 8
<211> LENGTH: 5
<212> TYPE: DNA
<213> ORGANISM: Homo sapiens

<400> SEQUENCE: 8 agctc                                                                     5
```

TISSUE SPECIFIC PROMOTERS AND TRANSGENIC MOUSE FOR THE SCREENING OF PHARMACEUTICALS

This application for a nonprovisional U.S. Utility Patent Application claims priority to Provisional U.S. patent application Ser. No. 60/106,495 filed on Oct. 30 1998.

This invention was supported in part by grants form the National Institutes of Health; number AR39750.

FIELD OF THE INVENTION

The present invention pertains to the identification and characterization of a nucleic acid sequence of the human involucrin gene which targets expression of any desired nucleic acid sequence to specific tissues and specific cells. In particular, this invention relates to nucleic acid sequences which target expression of nucleic acid sequences to suprabasal cells in stratifying squamous epithelial tissue and to uroepithelial cells. In another aspect, this invention pertains to transgenic animals which exhibit certain cancers and hyperplasias. In yet another aspect, this invention pertains to methods of screening for therapeutics for epithelial neoplasia.

BACKGROUND OF THE INVENTION

Diseases of epithelial cells are the single most common cause of morbidity and mortality of humans. Foremost among these diseases is cancer. Other diseases which are epithelial in origin include, for example, blistering disease (e.g., epidermolytic hyperkeratosis, and Dowling-Meara disease) proliferative disease (e.g., psoriasis, epidermal lysis, and Bulosa simplex) and Ichthyosis disease (e.g. Ichthyosis bullosa Simens, and recessive X-linked ichthyosis). The location of the epithelium as the lining of tissue surfaces in the body places it at a particularly high risk for repeated damage from a variety of agents in the environment. For example, most of the prevalent epithelial cancers (e.g., cancer of the lung, breast, colon, liver, cervix, etc.) are associated with exposure to carcinogens such as cigarette smoke, hydrocarbons in grilled foods, toxic molds, and infection with genital DNA tumor viruses.

The evaluation of candidate therapeutics directed at the treatment of epithelial disease has traditionally focused on animal models in which the animal is repeatedly exposed to one or a combination of chemicals. For example, models for cancer development and treatment rely on administration of carcinogenic and co-carcinogenic compounds. However, one drawback to such a model is that animals treated with chemicals exhibit a multitude of genetic and metabolic alterations. The multiplicity of genetic and metabolic changes makes it difficult to determine which of this multitude of changes is causally related to the resulting disease state, and hence makes it also difficult, if not impossible, to identify candidate therapeutics which target only relevant genetic and/or metabolic lesions. The further problems of unpredictability and variability of genetic and metabolic changes in response to chemical treatment make such animals poor models for the evaluation of therapeutics.

More recently, trangenic animals which harbor known genetic alterations and which express epithelial disease have been used. In particular, transgenic animal models which develop cancer and in which selected genes are expressed in epithelial cells in general (e.g., U.S. Pat. No. 5,550,316; Griep et al. (1994) Proc. Soc. Exp. Biol. Med. 206:24–34; Kondoh et al. (1995) Intervirology 38:181–186; Yang et al. (1995) Am J. Pathol. 147:68–78; Greenhalgh et al. (1994) Cell Growth Differ. 5:667–675; Tinsley et al. (1992) J. Gen. Virol. 73:1251–1260) have been described.

For example, the involvement of human papillomavirus (HPV) in cancer development has been investigated in model transgenic animals. Mice transgenic with HPV16 oncogenes express a number of malignancies (Table 1).

TABLE 1

Transgenic Animals Containing HPV-16-Oncogenes

| Promoter | Gene | Sites of mRNA or Protein Expression | Major Phenotype | References |
|---|---|---|---|---|
| Human keratin 14 | HPV-16 E7 | Epidermis; hair follicles; sebaceous glands. | Epidermal hyperplasia in skin, mouth palate, esophagus, forestomach, and exocervix; skin rumor. | Herber et al. (1996) J. Virol. 70:1873–1881 |
| Human β-actin | HPV-16 E6 and E7 | Epidermis; cervix; vagina. | Epidermal hyperplasia; cervical dysplasia; vaginal and cervical dysplasia and carcinoma in situ (17-β-estradiol). | Arbeit et al. (1996) Proc. Natl. Acad. Sci. USA 93:2930–2935. |
| Bovine thyroglobulin | HPV-16 E7 | Thyroid. | Differentiated goiters; invasive undifferentiated goiters. | Ledent et al. (1995) Oncogene 10:1789–1797 |
| αA-crystallin | HPV-16 E6 and E7 | Skin; eyes. | Squamous cell carcinoma; lenticular tumor. | Frazer et al. (1995) Cancer Res. 55:2635–2639. |
| MMTV | HPV-16 E6 and E7 | Cervix; vagina; salivary gland. | Cervical and vaginal dysplasia and hyperplasia; salivary gland carcinoma; lymphoma; skin histiocytoma. | Sasagawa et al. (1994) J. Gen. Virol. 75:3057–3065. |
| Bovine Keratin 6 | HPV-16 early region | Tongue; stomach; female reproductive tract; tail skin. | Metastatic stomach tumors. | Searle et al. (1994) J. Gen. Virol. 75:1125–1137. |

TABLE 1-continued

Transgenic Animals Containing HPV-16-Oncogenes

| Promoter | Gene | Sites of mRNA or Protein Expression | Major Phenotype | References |
|---|---|---|---|---|
| Human Keratin 14 | HPV-16 early region | Skin. | Ear epidermal hyperplasia and dysplasia; facial epidermal hyperplasia and papillamatosis; anal papilioma; truncal ulcers, diffuse epidermal hyperplasia; cataracts; lenticular hyperplasia. | Arbeit et al. (1994) J. Virol. 68:4358–4368. |
| Human keratin 14 | HPV-16 B6 and E7 | Skin. | Ear epidermal hyperplasia and dysplasia; facial epiedermal hyperplasia and papillomatosis; anal papillomas, truncal ulcers; cataracts; cervico-vaginal carinoma (17-β-estradiol). | Arbeit et al. (1994) WO/95/33820; Arbeit et al, (1994) WO 95/33826. |
| Human α-actin | HPV-16 E6 and E7. | Neuroepithelial tumors | Neuroepithelial carcinoma. | Arbeit et al. (1993) Am. J. Pathol. 142:1187–97. |
| αA-crystallin | HPV-16 E6 and E7 | Ocular lens; skin. | Bilateral microphthalmia and lens tumor; skin preneoplastic lesion and carcinoma. | Lambert et al. (1993) Proc. Natl. Acad, Sci. USA 90:5583–5587. |
| αA-crystallin | HPV-16 E6 and E7 | Ocular lens; eye without lens; brain, intestine, tail. | Lens tumor. | Griep et al. (1993) J. Virol. 67: 1373–84. |
| MMTV-LTR | HPV-16 E6 and E7 | Testicular tumor; submandibular gland. | Testicular tumor (seminoma). | Kondoh et al. (1991) J. Virol. 65:3335–3339. |

While there exist transgenic animals which develop epithelial cell disease in general, and neoplastic and/or preneoplastic lesions in particular, there is no transgenic model for some epithelial diseases (e.g., blistering disease, proliferative disease, and Ichthyosis disease) or for certain cancers (e.g., colon cancer, anal cancer, etc.). Furthermore, because the development of a single cancer phenotype may be caused by more than one genetic alteration, even those cancers for which there is available a transgenic animal model having a defined genetic lesion, such a single transgenic animal model is potentially of limited use in comprehensive screening of therapeutics. This is because a compound which is not therapeutic in a transgenic animal that has a particular genetic alteration, may nevertheless be therapeutic in a transgenic animal which develops the same disease as a result of a different genetic alteration.

Thus, there is a need for a better model of epithelial cell disease. This model should be amenable to identifying therapeutic compounds.

SUMMARY OF THE INVENTION

The present invention provides methods for selective expression of a nucleic acid sequence of interest in epithelial cells of a non-human transgenic animal, and in particular to suprabasal epithelial cells. This invention further relates to methods for producing a non-human transgenic animal wherein a nucleotide sequence of interest is selectively expressed in epithelial cells of the non-human animal, and more particularly in suprabasal epithelial cells. The present invention also relates to the use of the transgenic animals for screening anti-neoplastic compounds. Further provided by this invention are oligonucleotide sequences which selectively target expression of a nucleotide sequence of interest to epithelial cells, and in particular to suprabasal epithelial cells.

The present invention provides a purified oligonucleotide comprising at least a portion of the nucleotide sequence of FIG. 6 (SEQ ID NO:1) from nucleotide −2473 to −1953. While it is not intended that the present invention be limited to a particular type of activity of the portion of the nucleotide sequence of FIG. 6 (SEQ ID NO:1) from nucleotide −2473 to −1953, in one embodiment, the portion of oligonucleotide is characterized by having promoter activity. Furthermore, while it is not contemplated that the invention be limited to a particular portion of FIG. 6 (SEQ ID NO:1) from nucleotide −2473 to −1953, in a preferred embodiment, the portion of SEQ ID NO:1 comprises the entire nucleotide sequence from −2473 to −1953 of SEQ ID NO:1 or portions, variants or homologs thereof. In an alternative embodiment, the portion of FIG. 6 (SEQ ID NO:1) from nucleotide −2473 to −1953, or portions, variants or homologs thereof, is operably linked with nucleotide sequence −41 to −7 of FIG. 6 (SEQ ID NO:1), or portions, variants or homologs thereof.

While it is not contemplated that the invention be limited to encoding any particular peptide transcription factor binding sites, in a preferred embodiment, the sequence contains, at least, an AP1 (activator protein-1) site. In another embodiment, it is contemplated that the sequence contain any peptide transcription factor binding site or sites that allow for the expression of an operably linked nucleotide sequence. Although the invention is not contemplated to be limited to any particular peptide transcription factor binding sites, examples of such peptide transcription factor binding sites are Sp1, AP1-5 and AP1-1. It is additionally contemplated that one skilled in the art may substitute, add or delete any specific peptide transcription factor binding sites in the portion of FIG. 6 (SEQ ID NO:1) from nucleotide −2473 to −1953 for any other peptide transcription factor binding site.

In one embodiment of the present invention the portion of FIG. 6 (SEQ ID NO:1) from nucleotide −2473 to −1953 is operably linked to a nucleic acid sequence of interest. The invention is contemplated not to be limited to the type or nature of the nucleic acid sequence which is operably linked to the nucleotide sequence of the invention.

In another embodiment of this invention, the promoter activity of the portion of FIG. 6 (SEQ ID NO:1) from nucleotide −2473 to −1953 is tissue specific. While not intending to limit the invention to a particular type of tissue, in one embodiment, the tissue is selected from the group consisting of uroepithelial tissue and stratified squamous epithelial tissue. In a preferred embodiment, it is contemplated that the stratified squamous epithelial tissue is in an organ selected from the group consisting of epidermis and cervix. In yet a more preferred embodiment, the stratified squamous epithelial tissue specific promoter activity is cell type specific. In a further preferred embodiment, it is contemplated that the cell in the stratified squamous epithelial tissue is suprabasal.

The present invention also provides a recombinant expression vector comprising at least a portion of FIG. 6 (SEQ ID NO:1) from nucleotide −2473 to −1953. While it is not intended that the present invention be limited to the type of activity of portion of FIG. 6 (SEQ ID NO:1) from nucleotide −2473 to −1953, in one embodiment, the portion of the oligonucleotide is characterized by having promoter activity. Furthermore, while it is not contemplated that the invention be limited to a particular portion of FIG. 6 (SEQ ID NO:1) from nucleotide −2473 to −1953, in a preferred embodiment, the portion of SEQ ID NO:1 comprises the entire nucleotide sequence from −2473 to −1953 of SEQ ID NO:1 or portions, variants or homologs thereof. In an alternative embodiment, the portion of FIG. 6 (SEQ ID NO:1) from nucleotide −2473 to −1953, or portions, variants or homologs thereof, is operably linked with a portion of FIG. 6 (SEQ ID NO:1) from nucleotide −2473 to −1953, or portions, variants or homologs thereof.

Further provided by the present invention is a host cell comprising a recombinant expression vector wherein the recombinant expression vector comprises at least a portion of FIG. 6 (SEQ ID NO:1) from nucleotide −2473 to −1953. While it is not intended that the host cell be limited to a particular cell type, in a preferred embodiment, the host cell is a fertilized egg cell. In an alternative preferred embodiment, the host cell is in a blastomere. In a further preferred embodiment, the host cell is in an eight-cell embryo. In yet another preferred embodiment, the host cell is in a midgestation embryo. In yet a further preferred embodiment, the host cell is an embryonic stem cell.

The present invention further provides a transgenic non-human animal capable of tissue specific expression of a nucleic acid sequence of interest, wherein the transgenic non-human animal comprises an oligonucleotide comprising at least a portion of FIG. 6 (SEQ ID NO:1) from nucleotide −2473 to −1953 operably linked to the nucleic acid sequence of interest. While it is not intended that the invention be limited to a particular type of tissue, in a preferred embodiment, expression takes place in a tissue selected from the group consisting of stratified squamous epithelial tissue and uroepithelial tissue. Also without intending to limit the type of tissue in which expression occurs, in yet a more preferred embodiment, the stratified squamous epithelial tissue is in an organ selected from the group consisting of epidermis and cervix.

While it is not intended to limit the invention to any particular nucleic acid sequence of interest, in one embodiment, the nucleic acid sequence of interest is a coding sequence of an oncogene. In a more preferred embodiment, the oncogene is a human papillomavirus 16 oncogene. In yet a more preferred embodiment, the transgenic non-human animal is characterized by having cancer in a tissue selected from the group consisting of tracheal, esophageal, colon, epidermal, anal, rectal, lymph node, spleen, and lung tissue. In yet another preferred embodiment, the transgenic non-human animal is further characterized by having hyperplasia in a tissue selected from the group consisting of epidermal and cervical tissue.

Also provided by the invention is a method for selective expression of a nucleic acid sequence of interest in epithelial cells of a non-human animal, comprising: a) providing: i) a transgene, wherein the transgene contains at least a portion of the sequence set forth in FIG. 6 (SEQ ID NO:1) from nucleotide −2473 to −1953 operably linked to the nucleic acid sequence of interest; ii) an embryonic cell of a non-human animal; and iii) a pseudopregnant non-human animal; b) introducing: i) the transgene into the embryonic cell to produce a transgenic embryonic cell; and ii) the transgenic embryonic cell into the pseudopregnant non-human animal under conditions such that the pseudopregnant non-human animal delivers progeny derived from the transgenic embryonic cell, wherein the nucleic acid sequence of interest is selectively expressed in the epithelial cells of the progeny. In one embodiment, the method of the invention further comprises c) identifying at least one offspring of the progeny wherein the nucleic acid sequence of interest is selectively expressed in the epithelial cells of the offspring.

In another embodiment, a method is contemplated for the selective expression of a nucleic acid sequence of interest in epithelial cells wherein the transfected cell is a primary or transformed human or non-human epithelial cell. In one particular embodiment, said transformed epithelial cells are used for the screening of compounds that may inhibit or enhance the expression of said transfected gene of interest. In one embodiment, said method comprises: a) providing: i) a transgene, wherein the transgene contains at least a portion of the sequence set forth in FIG. 6 (SEQ ID NO:1) from nucleotide −2473 to −1953 operably linked to the nucleic acid sequence of interest; and ii) primary or transformed human or non-human epithelial cells; b) introducing the transgene into the primary or transformed human or non-human epithelial cells; c) contacting said transfected epithelial cells with the compound or compounds suspected of inhibiting or enhancing the expression of said transfected genes and/or the function of the expression products of said transfected genes; and d) determining the inhibition or enhancement of said transfected gene expression or function of said transfected gene expression product, if any. The invention is not limited to any particular transfection method. Many transfected methods are envisioned including electroporation, $CaCl_2$ transfection and lipofectamine transfection. The invention is not limited to any particular method of determining the inhibition or enhancement of said transfected gene expression or function of said transfected gene expression product. Many methods are contemplated including histological staining, Western blotting, Northern blotting, Southern blotting, electrophoresis, immunodetection, protein binding assays, PCR analysis, measurement of proliferation and/or apoptosis.

In another embodiment, a method is contemplated for the selective expression of a nucleic acid sequence of interest in cells obtained from a patient or from an immuno-compatible donor. In one embodiment, said transformed patient or donor cells are used for the expression of said transgene of interest in said patient for gene therapy. In one particular embodiment, said method comprises: a) providing: i) a transgene, wherein the transgene contains at least a portion of the sequence set forth in FIG. 6 (SEQ ID NO:1) from nucleotide −2473 to −1953 operably linked to the nucleic acid sequence of interest; and ii) cells obtained from a patient or immuno-compatible donor; b) introducing the transgene into the cells obtained from a patient or immuno-compatible donor to produce transfected cells; c) introducing at least a portion of said transfected cells into said patient; and c) monitoring said patient for expression of the transfected gene or gene product, if any, or for reduction or enhancement of the disease being treated by said gene therapy. The invention is not limited to any particular transfection method. Many transfected methods are envisioned including electroporation, $CaCl_2$ transfection and lipofectamine transfection. The invention is not limited to any particular disease or condition to be treated by this method of gene therapy. Any disease is a candidate for treatment by this method. In one embodiment, such diseases are of suprabasal epithelia cells.

Without intending to limit the invention to a particular portion of the sequence set forth in FIG. 6 (SEQ ID NO:1) from nucleotide −2473 to −1953, in one embodiment, the portion of SEQ ID NO:1 comprises the entire nucleotide sequence from −2473 to −1953 of SEQ ID NO:1 or portions, variants or homologs thereof. In an alternative embodiment, the portion of the sequence set forth in FIG. 6 (SEQ ID NO:1) from nucleotide −2473 to −1953 comprises the entire nucleotide sequence from −2473 to −1953 of SEQ ID NO:1, or portions, variants or homologs thereof, operably linked with the portion of the sequence set forth in FIG. 6 (SEQ ID NO:1) from nucleotide −41 to −7, or portions, variants or homologs thereof.

The present invention also provides a method for producing a non-human transgenic animal, comprising: a) providing: i) a transgene, wherein the transgene contains at least a portion of the sequence set forth in FIG. 6 (SEQ ID NO:1) from nucleotide −2473 to −1953 operably linked to one or more oncogenes; ii) an embryonic cell of a non-human animal; and iii) a pseudopregnant non-human animal; b) introducing: i) the transgene into the embryonic cell to produce a transgenic embryonic cell; and ii) the transgenic embryonic cell into the pseudopregnant non-human animal under conditions such that the pseudopregnant non-human animal delivers progeny derived from the transgenic embryonic cell; and c) identifying at least one offspring of the progeny, wherein the oncogene is selectively expressed in epithelial cells of the offspring.

While it is not intended that the invention be limited to the type of epithelial cell, in one embodiment, the epithelial cell is suprabasal. While not intending to limit the oncogene to a particular oncogene, in one embodiment, the oncogene consist of human papillomavirus 16 oncogene E6 nucleic acid sequence and oncogene E7 nucleic acid sequence. In a preferred embodiment, the non-human transgenic animal is further characterized by having cancer in one or more tissues selected from the group comprising trachea, esophagus, colon, epidermis, anus, rectum, lymph node, spleen and lung. In yet another preferred embodiment, the non-human transgenic animal is further characterized by having hyperplasia in one or more tissues comprising epidermis and cervix.

The present invention further provides a method of screening anti-neoplastic compounds, comprising: a) providing: i) a transgenic non-human animal having cancer, wherein the transgenic non-human animal contains a DNA sequence comprising at least a portion of the sequence set forth in FIG. 6 (SEQ ID NO:1) from nucleotide −2473 to −1953 or portions, variants or homologs of the nucleotide sequence; and ii) a compound suspected of having anti-neoplastic activity; b) administering the compound to the transgenic non-human animal to produce a treated transgenic non-human animal; and c) detecting anti-neoplastic activity in the treated transgenic non-human animal, thereby identifying the compound as anti-neoplastic. While not restricting the invention to a particular type of cancer, in one embodiment, the cancer is colon cancer. In another embodiment, the cancer is anal cancer.

The present invention contemplates at least a portion of the sequence set forth in FIG. 6 (SEQ ID NO:1) from nucleotide −2473 to −1953 wherein the AP1-5 site is mutated as shown in FIG. 9A and FIG. 9B.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIG. 6 shows the sequence (SEQ ID NO:1) of the hINV upstream regulatory region, from nucleotide −2473 to −1.

FIG. 6: SEQ ID NO:5) sites and surrounding sequence. The altered nuceotides in the mutant AP1-5 site (AP1-5 mm) are underlined (SEQ ID NO:8).

FIG. 11 is a color image showing the effect of AP1-5 mutation on hINV expression in cervix and esophagus.

FIG. 13 shows the nucleotide sequences of human papillomavirus type 16 genes E6 (SEQ ID NO:6) and E7 (SEQ ID NO:7).

DEFINITIONS

Figure 1:
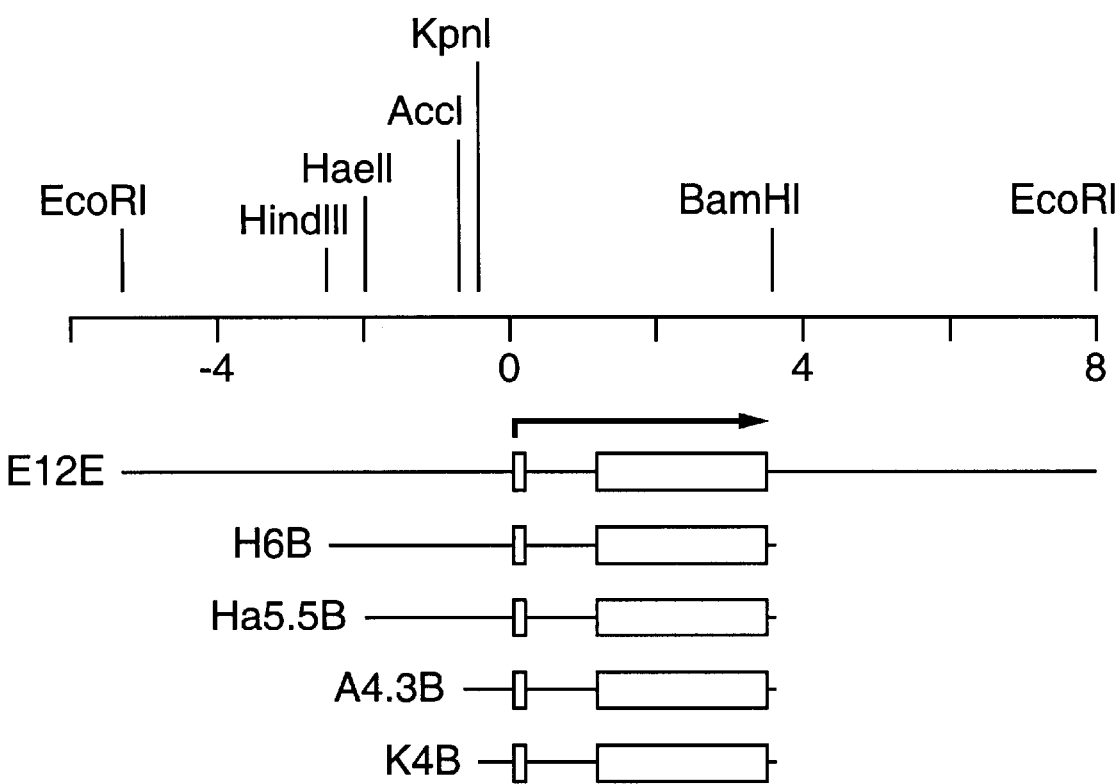
FIG. 1 shows schematic hINV transgene maps. The scale indicates length in kilobases relative to the transcription start site at zero. Distances are indicated as positive downstream and negative upstream of the transcription start site. The start, direction and extent of transcription are indicated by the arrow. Each construct is indicated by a narrow line. The small and black rectangles represent, respectively, the first and second exons. The constructs are named based on the restriction sites that were used in their constriction and the intervening number indicated the length of the DNA segment in kilobases (i.e. H6B is 6 kb HindIII/BamH1 fragment).

To facilitate understanding of the invention, a number of terms are defined below.

"Nucleic acid sequence", "nucleotide sequence" and "polynucleotide sequence" as used herein refer to an oligonucleotide or polynucleotide, and fragments or portions thereof, and to DNA or RNA of genomic or synthetic origin which may be single- or double-stranded, and represent the sense or antisense strand.

As used herein, the terms "oligonucleotides" and "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and of non-coding regulatory sequences do not encode an mRNA or protein product (e.g., promoter sequence, enhancer sequence, polyadenylation sequence, termination sequence, etc.).

"Amino acid sequence", "polypeptide sequence" and "peptide sequence" are used interchangeably herein to refer to a sequence of amino acids.

A "variant" of a first nucleotide sequence is defined as a nucleotide sequence which differs from the referenced, parent or wildtype nucleotide sequence e.g., by having one or more deletions, insertions, or substitutions that may be detected using hybridization assays or using DNA sequencing. Included within this definition is the detection of alterations to the genomic sequence of the first nucleotide sequence. For example, hybridization assays may be used to detect alterations in (1) the pattern of restriction enzyme fragments capable of hybridizing to a genomic sequence of the first nucleotide sequence (ie., RFLP analysis), (2) the inability of a selected portion of the first nucleotide sequence to hybridize to a sample of genomic DNA which contains the first nucleotide sequence (e.g., using allele-specific oligonucleotide probes), (3) improper or unexpected hybridization, such as hybridization to a locus other than the normal chromosomal locus for the first nucleotide sequence (e.g. using fluorescent in situ hybridization (FISH) to metaphase chromosomes spreads, etc.). One example of a varient is a mutated wildtype sequence.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, for example, the naturally occurring nucleotide or amino acid sequence.

A "substitution" results from the replacement of one or more nucleotides or amino acids by different nucleotides or amino acids, respectively.

The term "portion" when used in reference to a nucleotide sequence refers to fragments of that nucleotide sequence. The fragments may range in size from 5 nucleotide residues to the entire nucleotide sequence minus one nucleic acid residue.

An oligonucleotide sequence which is a "homolog" of a first nucleotide sequence is defined herein as an oligonucleotide sequence which exhibits greater than or equal to 50% identity, and more preferrably greater than or equal to 70% identity, to the first nucleotide sequence when sequences having a length of 25 bp or larger are compared.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region. Thus, the term "hINV upstream sequence" refers to a sequence which is located 5' of the human involucrin gene transcription start site, as exemplified by SEQ ID NO:1 depicted in FIG. 6.

The terms "hINV upstream nucleic acid sequence" and "hINV upstream nucleotide sequence" refer to at least a portion of the nucleotide sequence comprising the nucleotide sequence from −2473 to −1 of FIG. 6, and to variants, and homologs thereof.

The term "DRR" means distal regulatory region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics (i.e. ,particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (ie., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 68° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 μg/ml denatured salmon sperm DNA followed by washing in a solution comprising 2.0×SSPE, 0.1% SDS at room temperature when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formarnide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5×Denhardt's reagent and 100 μg/ml denatured salmon sperm DNA followed by washing in a solution comprising 0.1×SSPE and 0.1% SDS at 68° C. when a probe of about 100 to about 1000 nucleotides in lenght is employed.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of ) the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in *Nucleic Acid Hybridization* (1985)). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m°$ C. to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" the nucleotide sequence from positions −2473 and −1953 of FIG. 6 (SEG ID NO:1) or portions thereof will hybridize to its exact complement and closely related sequences. When portions of the nucleic acid sequence from positions −2473 and −1953 are employed in hybridization reactions, the stringent conditions include the choice of fragments of the nucleotide sequence from positions −2473 and −1953 of FIG. 6 (SEQ ID NO:1) to be used. Fragments of the nucleotide sequence from positions −2473 and −1953 of FIG. 6 (SEQ ID NO:1) which contain unique sequences (i.e., regions which are either non-homologous to or which contain less than 50% homology or complementarity with the nucleotide sequence from positions −2473 and −1953 of FIG. 6 (SEQ ID NO:1)) are preferentially employed. Conditions of "weak" or "low" stringency are often required with nucleic acids that are derived from organisms that are genetically diverse, as the frequency of complementary sequences is usually low between such organisms.

As used herein, the term "amplifiable nucleic acid" is used in reference to nucleic acids which may be amplified by any amplification method. It is contemplated that "amplifiable nucleic acid" will usually comprise "sample template."

The term "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced, but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction technologies well known in the art (Dieffenbach C W and G S Dveksler (1995) *PCR Primer, a Laboratory Manual*, Cold Spring Harbor Press, Plainview N.Y.). As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule", so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (ie., the sense strand) or double-stranded. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

Transcriptional control signals in eukaryotes comprise "enhancer" elements. Enhancers consist of short arrays of DNA sequences that interact specifically with cellular proteins involved in transcription (Maniatis, T. et al., (1987) Science 236:1237). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, J. et al., (1989) *Molecular Cloning: A Laboratory Manual*, 2nd ed., Cold Spring Harbor Laboratory Press, New York, pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter", "promoter element" or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (ie., upstream) of an oligonucleotide sequence whose transcription into mRNA it controls, and provides a site for specific binding by RNA polymerase and for initiation of transcription.

The terms "human involucrin promoter" and "hINV promoter" refer to a promoter sequence derived from the human involucrin gene. hINV promoter sequences are exemplified by, but not limited to, the nucleotide sequence from −2473 to −1953 of FIG. 6. Additionally, the sequence from −41 to −7 of FIG. 6 contains basel promoter activity such as the inclusion of the TATA box.

The term "promoter activity" when made in reference to a nucleic acid sequence refers to the ability of the nucleic acid sequence to initiate transcription of an oligonucleotide sequence into mRNA.

The term "tissue specific" as it applies to a promoter refers to a promoter that is capable of directing selective expression of an oligonucleotide sequence to a specific type of tissue in the relative absence of expression of the same oligonucleotide in a different type of tissue. For example, as disclosed herein, a promoter sequence located from positions −2473 to −1953 (FIG. 6) of the human involucrin gene is capable of directing selective expression of human involucim gene sequences in stratifying epithelia. Tissue specificity of a promoter may be evaluated by, for example, operably linking a reporter gene to the promoter sequence to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. Selectivity need not be absolute. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of an oligonucleotide sequence in a specific type of cell in the relative absence of expression of the same oligonucleotide sequence in a different type of cell within the same tissue. For example, a promoter sequence disclosed herein located from positions −2473 to −1953 (FIG. 6) of the human involucrin gene is capable of directing selective expression of human involucim gene sequences in stratifying epithelial cells. The term "cell type specific" when applied to a promoter also means a promoter capable of promoting selective expression of an oligonucleotide in a region within a single tissue. Again, selectivity need not be absolute. For example, as disclosed herein, the promoter sequence located from positions −2473 to −1953 (FIG. 6) of the human involucrin gene directs expression of a gene to the suprabasal region of ectocervical epithelium, and not to the basal region of the ectocervical epithelium. Cell type specificity of a promoter may be assessed using methods well known in the art, e.g., immunohistochemical staining as described herein. Briefly, tissue sections are embedded in paraffin, and paraffin sections are reacted with a primary antibody which is specific for the polypeptide product encoded by the oligonucleotide sequence whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

The terms "selective expression", "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "contiguous" when used in reference to two or more nucleotide sequences means the nucleotide sequences are ligated in tandem either in the absence of intervening sequences, or in the presence of intervening sequences which do not comprise one or more control elements.

The term "transfection" or "transfected" refers to the introduction of foreign DNA into a cell.

As used herein, the terms "nucleic acid molecule encoding", "nucleotide encoding", "DNA sequence encoding" and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligo-deoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al. (1989) *Molecular Cloning: A Laboratory Manual*, Cold Spring Harbor Press, NY, pp 9.31–9.58).

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligo-deoxyribonucleotide probe or DNA probe to detect RNA species complementary to the probe used. Northern blots are a standard tool of molecular biologists (J. Sambrook, J. et al. (1989) supra, pp 7.39–7.52).

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligo-ribonucleotide probe or RNA probe to detect DNA species complementary to the oligo-ribonucleotide probe used.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g. hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "substantially purified" refers to molecules, either nucleic or amino acid sequences, that are removed from their natural environment, isolated or separated, and are at least 60% free, preferably 75% free and more preferably 90% free from other components with which they are naturally associated. An "isolated polynucleotide" is, therefore, a substantially purified polynucleotide.

As used herein the term "coding region" when used in reference to a structural gene refers to the nucleotide sequences which encode the amino acids found in the nascent polypeptide as a result of translation of a mRNA molecule. The-coding region is bounded, in eukaryotes, on the 5' side by the nucleotide triplet "ATG" which encodes the initiator methionine and on the 3' side by one of the three triplets which specify stop codons (i.e., TAA, TAG, TGA).

The term "hINV coding region" as used herein refers to the sequence of exon 1, intron 1, and exon 2 of the human involucrin gene, which is located in a EcoRI-restricted Charon 4AλI-3 (Eckert and Green (1986) Cell 46:583–589)).

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g. transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "peptide transcription factor binding site" or "transcription factor binding site" refers to a nucleotide seqeunce which binds protein transcription factors and, thereby, controls some aspect of the expression of nucleic acid sequences. For example, Sp-1 and AP1 (activator protein 1) binding sites are examples of peptide transcription factor binding sites.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The tern "oncogene" refers to a gene which is capable of transforming a normal cell to a cancer cell. An oncogene may be a viral oncogene or a cellular oncogene. A "viral oncogene" may be an early gene of a DNA virus (e.g., polyomavirus, papillomavirus, T-cell leukemia virus), or a cellular proto-oncogene incorporated into the genome of a transducing retroviruses such that the cellular proto-oncogene (e.g., c-src) is activated into an oncogene (e.g., v-src). In contrast to a viral oncogene, a "cellular oncogene" is a mutated cellular gene formed in situ in the chromosome of a cell rather than introduced into the cell by a DNA virus or a transducing virus.

The term "cancer cell" refers to a cell undergoing early, intermediate or advanced stages of multi-step neoplastic progression as previously described (H. C. Pitot (1978) in "Fundamentals of Oncology", Marcel Dekker (Ed.), New York pp 15–28). The features of early, internmediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplastic cell" and is characterized by dividing without control and/or at a greater rate than a normal cell of the same cell type in the same tissue. Proliferation may be slow or rapid but continues unabated. A cell in the intermediate stages of neoplastic progression is referred to as a "dysplastic cell." A dysplastic cell resembles an immature epithelial cell, is generally spatially disorganized within the tissue and loses its specialized structures and functions. During the intermediate stages of neoplastic progression, an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive, i.e., they either invade adjacent tissues, or are shed from the primary site and circulate through the blood and lymph to other locations in the body where they initiate secondary cancers. The term "cancer" or "neoplasia" refers to a plurality of cancer cells.

The term "epithelial cell" refers to a cuboidal-shaped, nucleated cell which generally located on the surface of a tissue. A layer of epithelial cells generally functions to provide a protective lining and/or surface that may also be involved in transport processes. An epithelial cell is readily distinguished from a non-epithelial cell (e.g., muscle cell, nerve cell, etc.) using histological methods well known in the art.

The term "non-stratifying cell" refers to an epithelial cell in a non-stratifying epithelial tissue. A "non-stratifying epithelial tissue" refers to a tissue which contains only a single layer of epithelial cells. Non-stratifying epithelial tissue is exemplified by, but is not limited to, epithelia lining the oviduct, gall bladder, kidney ducts, blood vessels, salivary gland ducts, pancreatic ducts, urinary tract lumen, etc. Non-stratifying epithelial tissue, stratifying epithelial tissue, and stratified squamous epithelial tissue tissue are readily distinguished one from the other by histological methods well known in the art, e.g., where tissue sections are stained with hematoxylin & eosin, or another stain.

The term "stratifying cell" refers to an epithelial cell in a stratifying epithelial tissue. The terms "stratifying epithelial tissue", "stratified epithelial tissue" and "stratified squamous epithelial tissue" refer to a tissue containing two or more layers of epithelial cells wherein the epithelial cells undergo morphological and functional changes. Generally, a "stratified squamous epithelial tissue" contains a basal layer of epithelial cells, a supra basal layer of epithelial cells and a surface layer of epithelial cells. The basal layer is proximal to the organ lined by the stratified squamous epithelial tissue, the surface layer is distal to the lined organ, whereas the suprabasal layer is located between the basal layer and the surface layer. Stratified squamous epithelial tissue includes, but is not restricted to, ectocervix, vagina, epidermis, brachea, esophagus, cornea, etc The term "squamous cell" refers to an epithelial cell in a stratified squamous epithelial tissue. A squamous cell may be a basal cell, a suprabasal cell, or a surface cell. The terms "basal cell", "suprabasal cell" and "surface cell" refer, respectively, to a squamous epithelial cell which is located in the basal layer, suprabasal layer and surface layer of a stratified squamous epithelial tissue. A basal cell, suprabasal cell and surface cell are readily distinguishable on the basis of their morphology as determined, for example, by histochemical staining methods known in the art (e.g., Wheater et al., (1987) in "Functional Histology," 2nd Edition, Churchill/Livingstone (Eds.) New York, 303, pp 65–70). Basal epithelial cells are generally cuboidal, suprabasal cells are generally less cuboidal and more flattened than adjacent basal cells, while surface cells are more flattened than both basal cells and suprabasal cells of the same stratified squamous epithelial tissue.

The terms "uroepithelial cell" and "transitional epithelial cell" refer to an epithelial cell in the uroepithelial tissue. As used herein, the term "uroepithelial tissue" refers to epithelial tissue located at the renal pelvic area where the ureter meets with the kidney. Uroepithlial cells are unique to the urine conducting passage of the urinary system and are characterized by having a thickened plasma membrane.

A "non-human animal" refers to any animal which is not a human and includes vertebrates such as rodents, non-human primates, ovines, bovines, ruminants, lagomorphs, porcines, caprines, equines, canines, felines, aves, etc. Preferred non-human animals are selected from the order Rodentia.

The term "order Rodentia" refers to rodents, i.e., placental mammals (class Euthria) which include the family Muridae (e.g., rats and mice), most preferably mice.

A "transgenic animal" as used herein refers to an animal that includes a transgene which is inserted into a cell and which becomes integrated into the genome either of somatic and/or germ line cells of the. A "transgene" means a DNA sequence which is partly or entirely heterologous (i.e., not present in nature) to the animal in which it is found, or which is homologous to an endogenous sequence (i.e., a sequence that is found in the animal in nature) and is inserted into the animal's genome at a location which differs from that of the naturally occurring sequence. Transgenic animals which include one or more transgenes are within the scope of this invention.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by testing using the testing methods of the present invention. A "known therapeutic compound" refers to a therapeutic compound that has been shown (e.g., through animal trials or prior experience with administration to humans) to be effective in such treatment or prevention.

A compound is said to be "in a form suitable for administration such that the compound is bio-available in the blood of the animal" when the compound may be administered to an animal by any desired route (e.g., oral, intravenous, subcutaneous, intrathecal, intraperitoneal, intramuscular, etc.) and the compound or its active metabolites appears in the blood of the animal in an active form.

The terms "anti-neoplastic" and "anti-cancer" refer to a compound which arrests or retards the rate of neoplastic progression (e.g., cancer cell growth or proliferation). The term also refers to a compound which reduces the number of cancer cells in the absence of a change in the rate of neoplastic progression. Anti-neoplastic compounds may be naturally occurring as well as man-made.

"Differentiation-appropriate" and differentiation-specific" shall be defined herein as physiological events (e.g. gene expression) that are genetically determined to take place during the differentiation of cells or tissues. For example, the genes that are turned on and/or off during the differentiation of chondrocytes to osteoblasts is an example of differantiation-appropriate or differantiation-specific gene expression.

As used herein, "AP1-5" shall be defined as a transcription factor binding site with the following sequence: 5'-TGAGTCA-3'. As used herein, "SP-1" shall be defined as a transcription factor binding site with the sequence: 5'-GGGCGG-3'. As used herein, "AP1-5 mm" shall be defined as a mutated transcription factor binding site with the sequence: 5'-AGCTCCA-3'.

As used herein "agonist" refers to molecules or compounds which mimic the action of a "native" or "natural" compound. Agonists may be homologous to these natural compounds in respect to conformation, charge or other characteristics As used herein "antagonist" refers to molecules or compounds which inhibit the action of a "native" or "natural" compound. Antagonists may or may not be homologous to these natural compounds in respect to conformation, charge or other characteristics.

"Patient" shall be defined as a human or other animal, such as a guinea pig or mouse and the like.

GENERAL DESCRIPTION OF THE INVENTION

Epidermal keratinocytes undergo a program of differentiation that results in assembly of the epidermis (Green "The keratinocyte as differentiated cell type" *The Harvey Lectures* 74:101–139, 1980). This differentiation process involves a series of morphological and biochemical changes that are tightly controlled and involve specific temporal and spatial changes in gene expression (Green "The keratinocyte as differentiated cell type" *The Harvey Lectures* 74:101–139, 1980; Eckert, et al. "The epidermal keratinocyte as a model for the study of gene regulation and cell differentiation" *Physiol. Rev.* 77:397–424, 1997; Rice and Green "Presence in human epidermal cells of a soluble protein precursor of the cross-linked envelope: activation of the cross-linking by calcium ions" *Cell* 18:681–694, 1979). These changes include activation of the gene that encodes human involucrin (hINV). Involucrin is not expressed in the basal epidermal layer, but expression is activated in the late spinous layer and continues in the granular layer (Thatcher and Rice "Keratinocyte-specific transglutaminase of cultured human epidermal cells: relation to cross-linked envelope formation and terminal differentiation" *Cell* 40:685–695, 1985; Kim, et al. "Highly active soluble processed forms of the transglutaminase 1 enzyme in epidermal keratinocytes" *J. Biol. Chem.* 270:18026–18035, 1995). Involucrin in an a-helical, rod-shaped, 68 kilodalton glutamine- and glutamic acid-rich structural protein that is an efficient transglutaminase substrate (Steinert "Transglutaminase crosslinking and structural studies of the human small proline rich 3 protein" *Cell Death Differ* 2:33–40, 1999; Murphy, et al. "Involucrin expression in normal and neoplastic human skin: a marker for keratinocyte differentiation" *J Invest Dermatol* 82:453–457, 1984; Crish, et al. "Tissue-specific and differentiation-appropriate expression of the human involucrin gene in transgenic mice: an abnormal epidermal phenotype" *Differentiation* 53:191–200, 1993; Murthy, et al. "A dual role for involucrin in the epidermis-ultrastructural localization in epidermis and hair follicle in humans and transgenic mice" *J. Struct. Biol.* 111:68–76, 1993). During the final stages in keratinocyte differentiation, involucrin is incorporated, via the formation of interprotein ε-(γ-glutamyl)lysine cross-links with other proteins, into the keratinocyte cornified envelope (Steinert and Marekov "Direct evidence that involucrin is a major early isopeptide cross-linked component of the keratinocyte cornified cell envelope" *J. Biol. Chem.* 272:2021–2030, 1997). This envelope provides an essential protective barrier (Rice and Green "The cornified envelope of terminally differentiated human epidermal keratinocytes consists of cross-linked protein" *Cell* 11:417–422, 1977; Welter, et al. "Fos-related antigen (Fra-1), junB, and jund activate human involucrin promoter transcription by binding to proximal and distal AP1 sites to mediate phorbol ester effects on promoter activity" *J. Biol. Chem.* 270:12614–12622, 1995; Banks, et al. "Transcription factor Sp1 activates involucrin promoter activity in non-epithelial cell types" *Biochem. J.* 337:507–512, 1999). Involucrin plays a similar in other stratifying epithelia, including esophagus, cornea, ectocervix, vagina, etc. (Carroll, et al. "Tissue- and stratum-specific expression of the human involucrin promoter in transgenic mice" *Proc. Natl. Acad. Sci, USA* 90:10270–10274, 1993). In each tissue expression is confined to the suprabasal layers.

Identifying mechanisms that govern tissue-specific and differentiation-appropriate gene expression in stratifying epithelia, such as epidermis, is an area of intense interest. In these epithelia, stem cells give rise to daughter cells that then differentiate to form the suprabasal layers of the tissue. This process produces profound changes in cell morphological and biochemistry. Several marker proteins have been identified that are differentially regulated during this process, including loricrin (Bickenbach, et al. "Loricrin expression is coordinated with other epidermal proteins and the appearance of lipid lamellar granules in development" *J. Invest. Dermatol.* 104:405–410,1995), filaggrin (Dale, et al. "Expression of epidermal keratins and filaggrin during human fetal skin development" *J. Cell Biol.* 101:1257–1269, 1985), cornifin (Dale, et al. "Expression of epidermal keratins and filaggrin during human fetal skin development" *J. Cell Biol.* 101:1257–1269, 1985; Byme, et al. "Programming gene expression in developing epidermis" *Development* 120:2369–2383, 1994). Involucrin is a precursor of the cornified envelope, and, as such, is an early marker of karatinocyte differentiation (i.e., it's expression is differentiation-specific). In epidermis, involucrin is expressed in the late spinous layer and granular layer (Rice and Green "Presence in human epidermal cells of a soluble protein precursor of the cross-linked envelope: activation of the cross-linking by calcium ions" *Cell* 18:681–694, 1979; Crish, et al. "Tissue-specific and differentiation-appropriate expression of the human involucrin gene in transgenic mice: an abnormal epidermal phenotype" *Differentiation* 53:191–200, 1993; Warhol, et al. "Immuno-ultrastructural localization of involucrin in squamous epithelium and cultured keratinocytes" *J. Histochem. Cytochem.* 33:141–149, 1985); in ectocervix it is expressed in the layer immediately above the basal layer (Crish, et al. "Tissue-specific and differentiation-appropriate expression of the human involucrin gene in transgenic mice: an abnormal epidermal phenotype" *Differentiation* 53:191–200, 1993). Other genes, such as loricrin, are expressed later in the differentiation process (Mehrel, et al. "Identification of a major keratinocyte cell envelope protein, loricrin" *Cell* 61:1103–1112, 1990; DiSepio, et al. "The proximal promoter of the mouse loricrin gene contains a functional AP1 element and directs keratinocyte-specific but not differentiation-specific expression" *J. Biol. Chem.* 270:10792–10799, 1995).

Previous studies implicate activator protein 1 (Eckert, et al. "The epidermis: genes on—genes off" *J. Invest. Dermatol.* 109:501–509, 1997; Banks, et al. "Characterization of human involucrin promoter distal regulatory region transcriptional activator elements-a role for Sp1 and AP1 binding sites" *Biochem. J.* 331:61–68, 1998), Sp1 (Banks, et al. "Characterization of human involucrin promoter distal regulatory region transcriptional activator elements-a role for Sp1 and AP1 binding sites" *Biochem. J.* 331:61–68, 1998), POU (Welter, et al. "Regulation of human involucrin promoter activity by POU domain proteins" *J. Biol. Chem.* 271:14727–14733, 1996) and other factors (LaPres and Hudson "Identification of a functional determinant of differentiation-dependent expression in the involucrin gene" *J. Biol. Chem.* 271:23154–23160, 1996) as regulators of hINV promoter activity in cultured cells, and a previous transgenic study showed that the H6B construct (FIG. 1) can drive production of hINV in the epidermis and ectocervix of mice (Crish, et al. "Tissue-specific and differentiation-appropriate expression of the human involucrin gene in transgenic mice: an abnormal epidermal phenotype "*Differentiation* 53:191–200, 1993). However, the specific promoter region or regions were not discerned. H6B includes approximately 2.5 kb of DNA upstream of the transcription start site, the two exons, the intron and a short sequence segment downstream of the polyadenylation signal. Although the expression of this construct appeared physiologic, we wanted to test larger constructs to determine whether additional sequences would alter expression. The E13E results, disclosed herein, show that the presence of additional DNA does not change the regulation. Thus, neither the downstream region (+4500/+8000) nor the most distal upstream region (−5000/−2473) is required for appropriate expression in stratifying epithelia. To identify regions that are important for expression, we tested promoter deletions. In contrast to E13E and H6B, Ha5.5B is not expressed in epidermis, cervix or other stratifying epithelia, suggesting that elements within the 520-bp −2473/−1953 DRR segment (Banks, et al. "Characterization of human involucrin promoter distal regulatory region transcriptional activator elements-a role for Sp1 and AP1 binding sites" *Biochem. J.* 331:61–68, 1998) are essential for this expression. Truncation of additional sequence, in constructs A4.3B and P3.4B, does not restore expression. The loss of expression was not because of a general inactivation of the promoter. Except for P3.4B, these constructs retain expression in kidney. Only expression of P3.4B was turned off in all tissues tested, suggesting that the −41 to −7 bp of upstream region present in this construct represents the basal promoter. This region includes only the TATA box and some associated sequences (FIG. 6). Thus, the hINV promoter appears to be organized into modular units including a "stratifying epithelial module" located in the distal regulatory region (DRR) of the promoter, a kidney module located from nucleotides −986 to −41 and a basel promoter located from nucleotides −41 to −7 of FIG. 6.

Splicing the DRR segment upstream of P3.4B, the basal promoter construct, restores expression in stratifying epithelia. This result suggests that the DRR segment is necessary for expression in stratifying epithelia and that the −1953/−41 segment is not required for such expression. However, without limiting the invention to any particular mechanism, it could be argued that the DRR region may be acting in conjunction with DNA in the transcribed region of the gene (e.g. the intron). However, the hINV promoter (from nucleotides −2473 to −1953 of FIG. 6) also drives stratifying epithelia-specific expression of heterologous genes (Carroll, et al. "Tissue- and stratum-specific expression of the human involucrin promoter in transgenic mice" *PNAS* 90:10270–10274, 1993). The smallest construct tested, the −2473/−41 segment, also drives expression of heterologous genes in stratifying epithelia. Taken together, these results suggest that the DRR is both necessary and sufficient for expression in stratifying epithelia.

Although the DRR is necessary and sufficient for expression, other sequences appear to be necessary to produce cell type specific expression. In the absence of the −1953/−41 segment, the DRR produces expression only in the extreme suprabasal cell layers. This suggests that interaction between elements in the DRR and in the −1953/−41 segment may be required for expression in the layers immediately suprabasal to the stem cell layer.

The present investigation focuses on the ectocervical epithelia and epidermal epithelia. However, we also have checked several other surface epithelia to determine whether the DRR is generally required for expression. We have studied esophagus, epidermis, footpad, ectocervix and trachea. In each case, the DRR is required for expression, indicating that the DRR is a generally required element for surface epithelial expression.

DNA sequence analysis indicates that the DRR contains binding sites for several transcription factors, in including functionally important Sp1 and AP1 sites (Welter, et al. "Fos-related antigen (Fra-1), junB, and junD activate human involucrin promoter transcription by binding to proximal and distal AP1 sites to mediate phorbol ester effects on promoter activity" *J. Biol. Chem.* 270:12614–12622, 1995; Banks, et al. " Characterization of human involucrin promoter distal regulatory region transcriptional activator elements-a role for Sp1 and AP1 binding sites" *Biochem. J.* 331:61–68, 1998; Efimova, et al. "Regulation of human involucrin promoter activity by a protein kinase C, Ras, MEKK1, MEK3, p38/RK, AP1 signal transduction pathway" *J. Biol. Chem.* 272:24387–24395, 1998). Our previous in vitro studies show that the basal promoter does not drive expression in karatinocytes; however, addition of the DRR restores hINV promoter activity (Banks, et al. "Characterization of human involucrin promoter distal regulatory region transcriptional activator elements-a role for Sp1 and AP1 binding sites" *Biochem. J.* 331:61–68, 1998). Moreover, mutation of the AP1 site (AP1-5) inactivates the promoter (see, e.g., Examples 7–9). AP1 has been shown to be an important regulator in several genes that are expressed in a differentiation-dependent manner in surface epithelia (DiSepio, et al. "The proximal promoter of the mouse loricrin gene contains a functional AP1 element and directs keratinocyte-specific but not differentiation-specific expression" *J. Biol. Chem.* 270:10792–10799, 1995; Takahashi and Iizuka "Analysis of the 5'-upstream promoter region of human involucrin gene: activation by 12-O-tetradecanoylphorbol-13-acetate" *J. Invest. Dermatol.* 100:10–15, 1993). With out limiting the present invention to any mechanism, the present investigation shows that the AP1 site contained within the nucleotide sequence from −2473 to −1953 of FIG. 6 is important in the regulation of expression of the hINV gene as well as any sequences that may be operably linked to said sequence.

DETAILED DESCRIPTION OF PREFERRED EMBODIMENTS

The present invention provides sequences having tissue specific and cell type specific promoter activity. The sequences provided herein direct expression to suprabasal cells of stratifying epithelia. Also provided by the invention are methods for selectively targeting expression of a gene to a specific tissue and/or a specific cell type at a specific developmental stage within that tissue. These methods provide models for disease as well as for disease therapy and prevention.

In one embodiment, the invention provides transgenic animals in which hINV promoter sequences control the expression of the hINV coding region such that expression is selectively directed to suprabasal cells of certain tissues and not of other tissues. In another embodiment, the trangenic animals of the invention may contain a hINV promoter sequence which directs the expression of human papillomavirus 16 oncogenes. These animals display cervical and epidermal hyperplasias as well as cancer of the trachea, esophagus, colon, epidermis, anus/rectum, lymph nodes, spleen and lung. The animals of the invention provide a useful model for screening potential anti-neoplastic compounds, carcinogens, and co-carcinogens for a number of cancers.

The description of the invention is divided into (a) tissue specific and cell specific promoter sequences, (b) methods for selective gene expression and (c) uses for the transgenic animals.

A. Tissue Specific and Cell Specific Promoter Sequences

The present invention provides portions of the nucleic acid sequence (SEQ ID NO:1) of a sequence from −2473 to −1 of the hINV gene (FIG. 6) (the position numbers are designated in relation to the hINV start codon (ATG) in which the adenine is designated as position zero).

The present invention is not limited to a sequence from −2473 to −1953 of SEQ ID NO:1 but additionally contemplates portions thereof. It is preferred that the portions have a length equal to or greater than 10 nucleotides and show greater than 50% homology (and more preferrably greater than 70% homology) to a sequence from −2473 to −1953 of SEQ ID NO:1. In one embodiment, the invention comprises the nucleotide sequence from −2473 to −1953 of SEQ ID NO:1, or portions, variants or homologs thereof In an alternative embodiment the invention comprises the nucleotide sequence from −2473 to −1953 of SEQ ID NO:1, or portions, variants or bomologs thereof, operably linked with the nucleotide sequence from −41 to −7 of SEQ ID NO:1, or portions, variants or homologs thereof.

The sequences of the present invention are not limited to the nucleotide sequences −2473/−1953 and −41/−7 of SEQ ID NO:1 but include variants of these sequences and portions of these variants. These variants include, but are not limited to, nucleotide sequences having deletions, insertions or substitutions of different nucleotides or nucleotide analogs. Such variants may be produced using methods well known in the art.

The present invention is not limited to the nucleotide sequences −2473/−1953 and −41/−7 of SEQ ID NO:1 but is contemplated to include within its scope homologs of the nucleotide sequences −2473⎯1953 and −41/−7 of SEQ ID NO:1 and portions of these homologs and of variants of these homologs. Homologs which are capable of hybridizing to the nucleotide sequences −2473/−1953 and −41/−7 of SEQ ID NO:1 and portions thereof may be identified by hybridization at different stringencies. Those skilled in the art know that whereas higher stringencies may be preferred to reduce or eliminate non-specific binding between the nucleotide sequences −2473/−1953 and −41/−7 of SEQ ID NO:1 and other nucleic acid sequences, lower stringencies may be preferred to detect a larger number of nucleic acid sequences having different homologies to the nucleotide sequences −2473/−1953 and −41/−7 of nucleotide sequence of SEQ ID NO:1.

The invention provided herein is not limited to the nucleotide sequences −2473/−1953 and −41/−7 of SEQ ID NO:1, portions, variants, or homologs thereof having promoter activity, but includes sequences having no promoter activity. This may be desirable, for example, where a fragment of the nucleotide sequences −2473/−1953 and −41/−7 of SEQ ID NO:1 is used to detect the presence of the nucleotide sequences −2473/−1953 and −41/−7 of SEQ ID NO:1 or portions thereof in a sample by hybridizing the fragment with nucleic acid sequences in the sample.

The sequences of the invention are not limited to the nucleotide sequences −2473/−1953 and −41/−7 of SEQ ID NO:1, portions, variants, or homologs thereof whose promoter activity is both tissue specific and cell type specific. Rather, sequences having either cell type specific or tissue specific activity are also contemplated to be within the scope of the invention. These sequences are useful, for example, where it is desirable to target expression of a gene to suprabasal cells in a multiplicity of tissues, or to a multiplicity of tissues without regard to the type of cell targeted. Also expressly contemplated to be within the scope of the present invention are portions, variants and homologs of the nucleotide sequences −2473/−1953 and −41/−7 of SEQ ID NO:1 whose promoter activity is neither cell specific nor tissue specific. Such sequences are useful where expression of a gene is desired without regard to either the tissue or cell type in which it is expressed. For example, it may be desirable to express a gene in vitro in order to produce a protein product of the gene of interest for the purpose of purifying the protein and raising antibodies against the protein for diagnostic or therapeutic purposes. Expression in vitro may be accomplished by operably ligating the gene of interest to sequences of the invention and introducing the ligated expression construct into a cell. Expression in vitro may be detected using methods well known in the art, such as detection of the mRNA sequence (e.g., by Northern analysis) and/or of the polypeptide sequence (e.g., by antibody binding) encoded by the gene.

The present invention is not limited to sense molecules of the nucleotide sequences −2473/−1953 and −41/−7 of SEQ ID NO:1 but contemplates within its scope antisense molecules comprising a nucleic acid sequence complementary to at least a portion of the polynucleotide of the nucleotide sequences −2473/−1953 and −41/−7 of SEQ ID NO:1. These antisense molecules find use in, for example, reducing or preventing expression of a gene whose expression is controlled by the nucleotide sequences −2473/−1953 and 41/−7 of SEQ ID NO:1.

The nucleotide sequence of −2473/−1953 and −41/−7 of SEQ ID NO:1, portions, variants, homologs and antisese sequences thereof can be synthesized by synthetic chemistry techniques which are commercially available and well known in the art (see Caruthers M H et al., (1980) Nuc. Acids Res. Symp. Ser. 215–223; Horn T. et al., (1980) Nuc. Acids Res. Symp. Ser. 225–232). Additionally, fragments of the nucleotide sequences −2473/−1953 and −41/−7 of SEQ ID NO:1 can be made by treatment of the nucleotide sequences −2473/−1953 and −41/−7 of SEQ ID NO:1 with restriction enzymes followed by purification of the fragments by gel electrophoresis. Alternatively, sequences may also be produced using the polymerase chain reaction (PCR) as described by Mullis (U.S. Pat. No. 4,683,195) and Mullis el al. (U.S. Pat. No. 4,683,202), the ligase chain reaction (LCR; sometimes referred to as "Ligase Amplification Reaction" (LAR)) described by Barany, (1991) Proc. Natl. Acad. Sci., 88:189; Barany, (1991) PCR Methods and Applic., 1:5; and Wu and Wallace, (1989) Genomics 4:560. Fragments of the hINV upstream sequence may be ligated to each other or to heterologous nucleic acid sequences using methods well known in the art.

The nucleotide sequence of synthesized sequences may be confirmed using commercially available kits as well as using methods well known in the art which utilize enzymes such as the Klenow fragment of DNA polymerase 1, Sequenase®, Taq DNA polymerase, or thermostable T7 polymerase. Capillary electrophoresis may also be used to analyze the size and confirm the nucleotide sequence of the products of nucleic acid synthesis, restriction enzyme digestion or PCR amplification.

It is readily appreciated by those in the art (upon reading the teachings of the present specification) that the sequences of the present invention may be used in a variety of ways. For example, fragments of the sequence of at least about 10 bp, more usually at least about 15 bp, and up to and including the entire (i.e., full-length) sequence can be used as probes for the detection and isolation of complementary DNA sequences. This may be desirable, for example, to determine whether a construct containing sequences of the invention has been integrated into a cell.

The sequences provided herein are also useful in directing the synthesis of polypeptide sequences in vitro and in vivo. This is useful in determining the role of the polypeptide in disease development or treatment, as well as in producing antibodies for diagnostic or therapeutic purposes.

B. Methods for Selective Gene Expression

The present invention provides methods for selectively expressing a nucleotide sequence of interest in a particular cell type and/or a particular tissue. More specifically, the methods provided herein direct expression to stratifying epithelial cells. Yet more specifically, the stratifying epithelial cells are suprabasal cells. In one embodiment, this is accomplished by introducing into an animal cell a vector that contains a nucleotide sequence of interest operably linked to sequences provided herein which have tissue specific and/or cell specific promoter activity. The transfected animal cell is allowed to develop into a transgenic animal in which the nucleotide sequence of interest is expressed in selected cell types and/or tissues. These steps are further described below for specific embodiments.

1. Constructs

In one embodiment of the methods of the invention for directing expression of a nucleotide sequence of interest to specific cell types and/or tissues, a vector is constructed in which a promoter sequence from −2473 to −1953 or from −2473 to −1953 in operable combination with the sequenc −41 to −7 of FIG. 1 is operably linked to a nucleotide sequence of interest. In a preferred embodiment, the nucleotide sequence of interest is the open reading frame of HPV-16 E6 (GENBANK accession no. AJ388069, FIG. 13 nucleotides from 170 to 625; SEQ ID NO:6) and HPV-16 E7 (GENBANK accession no. AJ388069, FIG. 13 nucleotides from 628 to 921; SEQ ID NO:7) oncogenes. In another preferred embodiment the nucleotide sequence of interest is the coding region of the hINV gene.

The invention is not limited to the use of the portion of the sequence of FIG. 6 from −2473 to −1953 (SEQ ID NO:1). As noted above, a combination of two or more portions of the sequence of FIG. 6 are expressly contemplated to be within the scope of the invention. For example, where a first portion of the nucleotide sequence of FIG. 6 is determined to selectively direct expression of to a first tissue, and a second portion of the nucleotide sequence FIG. 6 SEQ ID NO:1 is determined to selectively direct expression of a nucleotide sequence to a second tissue, a combination of the first and second portions may be desirable to drive expression of a nucleotide sequence of interest in both the first and second tissues. An example of a portion of SEQ ID NO:1 which is tissue specific is a 520 bp sequence located from positions −2473 to −1953. Evidence presented herein demonstrates that this 520 bp sequence specifically directs expression of an operably linked sequence to the epidermis and ectocervix. Additionally, the present invention directs expression on an operably linked sequence to the basal epithelial cells of the epidermis and ectocervix.

The invention is not limited to coding regions of the HPV-16 E6/E7 gene or to the hINV gene. Any nucleic acid sequence whose expression is desired to be under the control of sequences provided herein is contemplated to be within the scope of this invention. Such nucleic acid sequences include, but are not limited to, coding sequences of structural genes (e.g., reporter genes, selection marker genes, oncogenes, drug resistance genes, growth factors, etc.), and of regulatory genes (e.g., activator protein 1 (AP1), activator protein 2 (AP2), Sp1, etc.). Additionally, such nucleic acid sequences may include non-coding regulatory elements which do not encode an mRNA or protein product. For example, it may be desirable to place a heterologous promoter which is derived from other than the hINV gene in tandem with promoter sequences of the present invention. Such chimeric promoters are included within the scope of the invention and may be desirable where, for example, chimeric promoters result in increased levels of expression of an operably linked downstream coding sequence. Chimeric promoters are known in the art and include, for example, the double Tet promoter (Kistner et al. (1996) Proc. Natl. Acad. Sci. USA 93:10933–10938), the U1 snRNA promoter-CMV promoter/enhancer (Bartlett et al. (1996) Proc. Natl. Acad. Sci. USA 93:8852–8857).

The invention is not limited to nucleotide sequences of interst which comprise a single coding sequence and/or a single non-coding regulatory element. A plurality (i.e., more than one) of coding and non-coding regions which are derived from a plurality of genes may be ligated in tandem such that their expression is controlled by the promoter sequences of the invention. A plurality of coding sequences may be desirable, for example, where it is useful to express a transcription product of more than one gene to permit interaction of these transcriptional products. In one embodiment, the open reading frames (ORFs) of the E6 oncogne (SEQ ID NO:6) and E7 oncogne (SEQ ID NO:7) of HPV-16 are ligated such that their expression is controlled by an hINV promoter sequence of the invention. One of skill in the art will recognize that the E6 and E7 ORF sequences may be modified by previously described methods (e.g., Sambrook et al., (1989) supra; Methods in Enzymology (1987) Vol. 152, Guide to Molecular Cloning Techniques (Berger and Kimmerl (Eds.), San Diego: Academic Press, Inc.)

Alternatively, a plurality of coding sequences may be desirable where one of the gene sequences is a reporter gene sequence. For example, it may be advantageous to place a coding sequence of a reporter gene in tandem with the coding sequence of a gene of interest such that expression of the coding region of both the reporter gene and the gene of interest is controlled by the promoter sequences of the invention. Expression of the reporter gene usually correlates with expression of the gene of interest. Examples of reporter gene sequences include the sequences encoding the enzymes β-galactosidase and luciferase.

Fusion genes may also be desirable to facilitate purification of the expressed protein. For example, the heterologous sequence which encodes protein A allows purification of the fusion protein on immobilized immunoglobulin. Other affinity traps are well known in the art and can be utilized to advantage in purifying the expressed fusion protein. For example, pGEX vectors (Promega, Madison Wis.) may be used to express the polypeptides of interest as a fusion protein with glutathione S-transferase (GST). In general, such fusion proteins are soluble and can easily be purified from lysed cells by adsorption to glutathione-agarose beads followed by elution in the presence of free glutathione. Other fusion polypeptides useful in the purification of the coiled coil polypeptide are commercially available, including histidine tails (which bind to $Ni^{2+}$), biotin (which binds to streptavidin), and maltose-binding protein (MBP) (which binds to amylose). Proteins made in such systems are designed to include heparin, thrombin or factor XA protease cleavage sites so that the cloned polypeptide of interest can be released at will from the heterologous polypeptide moiety to which it is fused.

One of skill in the art would understand that where a plurality of nucleic acid sequences of interest is operably linked to a promoter sequence of the present invention, the nucleic acid sequences of interest may be either contiguous or separated by intervening polynucleotide sequences, so long as the nucleic acid sequences of interest are placed in-frame.

Expression vectors in which expression of a nucleic acid sequences of interest is controlled by promoter sequences of the invention may be constructed using techniques well known in the art. (Sambrook et al. (1989) *Molecular Cloning, A Laboratory Manual*, Cold Spring Harbor Press, Plainview N.Y.; Ausubel et al. (1989) *Current Protocols in Molecular Biology*, John Wiley & Sons, New York N.Y.). Briefly, the nucleic acid sequences of interest is placed in operable combination with the hINV promoter sequences of the invention in the presence of transcription and translation regulatory sequences.

Regulatory sequences include initiation signals such as a start codon (i.e., ATG), enhancers, and transcription termination signals. The ATG initiation codon must be in the correct reading frame to ensure translation of the entire heterologous nucleotide sequence. Transcription termination signals are placed downstream of the heterologous nucleic acid sequence and include polyadenylation sequences which are exmplified by, but not limited to, SV40 poly-A sequence, hINV poly-A sequence, or bovine growth hormone poly-A sequence, etc. In a preferred embodiment, the initiation signals are those of the heterologous nucleotide sequence. Also in a preferred embodiment, the polyadenylation signal of SV40 is used.

Other regulatory sequences which may affect RNA stability as well as enhancers (i.e., a sequence which when activated resutls in an increase in the basal rate of transcription of a gene) and silencers (i.e., a sequence involved in reducing expression of a gene) may also be included. These regulatory sequences may be relatively position-insensitive, i.e., the regulatory element will function correctly even if positioned differently in relation to the heterologous nucleotide sequence in the construct as compared to its position in relation to the corresponding heterologous nucleotide sequence in the genome. For example, an enhancer may be located at a different distance from the hINV promoter sequence, in a different orientation, and/or in a different linear order. Thus, an enhancer that is located 3' to a hINV promoter sequence in germline configuration might be located 5' to the hINV promoter sequence in the construct.

It is not intended that the invention be limited to the type, number or location of regulatory sequences in constructs which contain hINV upstream sequences of the invention. One of skill in the art would understand that any number, type and location of regulatory sequences may be used with the sequences of the present invention provided that such regulatory sequences do no substantially interfere with the desired activity (e.g., promoter activity, tissue specific promoter activity, cell type specific promoter activity, ability to hybridize to homologous nucleotide sequences, etc.) of the sequences of the invention.

2. Host Cells

In order to bring about tissue specific and/or cell type specific expression, the expression vector which contains the hINV promoter sequences of the invention in operable combination with a nucleic acid sequences of interest is transfected into a host cell. Host cells include bacterial, yeast, plant, insect, and mammalian cells. In a preferred embodiment the host cell is mammalian. In a more preferred embodiment, the host cell is a mouse cell.

Any number of selection systems may be used to recover transfected cell lines. These include, but are not limited to, the herpes simplex virus thymidine kinase (Wigler M et al. (1977) Cell 11:223–32) and adenine phosphoribosyltransferase (Lowy I et al. (1980) Cell 22:817–23) genes which can be employed in tk or aprt cells, respectively. Also, antimetabolite, antibiotic or herbicide resistance can be used as the basis for selection; for example, dhfr which confers resistance to methotrexate (Wigler M et al., (1980) Proc Natl Acad Sci 77:3567–70); npt, which confers resistance to the aminoglycosides neomycin and G-418 (Colbere-Garapin F et al., (1981) J. Mol. Biol. 150:1–14) and als orpat, which confer resistance to chlorsulfiron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of a reporter gene system which expresses visible markers has gained popularity with such markers as β-glucuronidase and its substrate (GUS), luciferase and its substrate (luciferin), and β-galactosidase and its substrate (X-Gal) being widely used not only to identify transformants, but also to quantify the amount of transient or stable protein expression attributable to a specific vector system (Rhodes C A et al. (1995) Methods Mol Biol 55:121–131).

Although the presence or expression of the reporter gene usually indicates the presence or expression, respectively, of the tandem heterologous nucleic acid sequence as well. However, it is preferred that the presence and expression of the desired heterologous nucleic acid sequence be confirmed. This is accomplished by procedures known in the art which include DNA-DNA or DNA-RNA hybridization or amplification using probes, or fragments of the heterologous nucleic acid sequence. For example, Fluorescent In Situ Hybridization (FISH) can be used to detect the heterologous nucleic acid sequence in cells. Several guides to FISH techniques are available, e.g., Gall et al. Meth. Enzymol. 21:470–480 (1981); Angerer et al., in "Genetic Engineering: Principles and Methods," Setlow & Hollaender, Eds. Vol. 7 pp. 43–65, Plenum Press, New York (1985). Alternatively, DNA or RNA can be isolated from cells for detection of the transgene by Southern or Northern hybridization or by amplification based assays. Nucleic acid amplification based assays involve the use of oligonucleotides or oligomers based on sequence of the nucleic acid sequence of interest in order to detect cells and tissues which contain the DNA or RNA encoding the transgene of interest. Standard PCR methods useful in the present invention are described by Innis et al. (Eds.), "PCR Protocols: A Guide to Methods and Applications," Academic Press, San Diego (1990)).

Yet another alternative for the detection of heterologous nucleic acid sequences is by detecting the polypeptide product of transcription of the heterologous nucleotide sequence. A variety of protocols which employ polyclonal or monoclonal antibodies specific for the protein product are known in the art. Examples include enzyme-linked immunosorbent assay (ELISA), radioimmunoassay (RIA) and fluorescent activated cell sorting (FACS). A competitive binding assay may also be used. Alternatively, a two-site, monoclonal-based immunoassay which utilizes monoclonal antibodies that are reactive to two non-interfering epitopes on the protein of interest may be employed. These and other assays are described in, among other places, Hampton R et al. (1990), *Serological Methods a Laboratory Manual*, APS Press, St Paul Minn.), and Maddox D E et al. (1983), J. Exp. Med. 158:1211.

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the nucleic acid sequence of interest, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like.

3. Transgenic Animals

The present invention provides a number of transgenic animals. In one embodiment, transgenic animals are provided in which expression of any nucleic acid sequences of interest is selectively targeted to lurminal epithelial cells of the kidney in the presence/absence of expression in suprabasal cells of the epidermis, cervix, etc. These animals provide useful models for the identification of potential carcinogens and co-carcinogens which impact epithelial cells, identification of anti-neoplastic compounds and identification of genes which play a role in neoplastic progression of cancers of epithelial cells such as those in the trachea, esophagus, colon, epidermis, anus/rectum, lymph nodes, spleen, lung, and cervix.

In another embodiment, a construct (i.e., hINV-HPV16) may be produced in which the hINV upstream sequence from positions −2473/−1953 and −41/−7 may be placed contiguously upstream of the open reading frames of human papillomavirus 16 (HPV-16) oncogenes E6 and E7. This construct may be used to generate trangenic mice which express E6 and E7 mRNA in a tissue-specific and differentiation appropriate manner. Thus, full-length and spliced E6 and E7 mRNA may be expressed in stratifying epithelial tissue, such as the skin, cervix and urothelial lining. Moreover, E6 and E7 mRNA expression may be localized in suprabasal cells and not in the less differentiated contiguous basal cells of the same tissue. Transgenic mice which are heterozygous for the hINV-HPV16 construct will develop neoplasias of the trachea, esophagus, colon, epidermis, anus/rectum, lymph nodes, spleen and lung, as well as epidermal and ectocervical hyperplasias by the age of 7 months.

A first step in the generation of the transgenic animals of the invention is the introduction of a construct containing the desired heterologous nucleic acid sequence under the expression control of hINV upstream sequences of the invention into target cells. Several methods are available for introducing the expression vector which contains the heterologous nucleic acid sequence into a target cell, including microinjection, retroviral infection, and implantation of embryonic stem cells. These methods are discussed as follows.

i. Microinjection Methods

Direct microinjection of expression vectors into pronuclei of fertilized eggs is the preferred, and most prevalent, technique for introducing heterologous nucleic acid sequences into the germ line (Palmiter (1986) Ann. Rev. Genet. 20:465–499). Technical aspects of the microinjection procedure and important parameters for optimizing integration of nucleic acid sequences have been previously described (Brinster et al., (1985) Proc. Natl. Acad. Sci. USA 82:4438–4442; Gordon et al., (1983) Meth. Enzymol. 101:411–433; Hogan et al., (1986) Manipulation of the Mouse Embryo: A Laboratory Manual. Cold Spring Harbor, N.Y.: Cold Spring Harbor Lab.).

Once the expression vector has been injected into the fertilized egg cell, the cell is implanted into the uterus of a pseudopregnant female and allowed to develop into an animal. Of the founder transgenic animals born, 70% carry the expression vector sequence in all of their cells, including the germ cells. The remaining 30% of the transgenic animals are chimeric in somatic and germ cells because integration of the expression vector sequence occurs after one or more rounds of replication. Heterozygous and homozygous animals can then be produced by interbreeding founder transgenics. This method has been successful in producing transgenic mice, sheep, pigs, rabbits and cattle (Jaenisch (1988) supra; Hammer et al., (1986) J. Animal Sci.:63:269; Hammer et al., (1985) Nature 315:680–683; Wagner et al., (1984) Theriogenology 21:29).

ii. Retroviral Methods

Retroviral infection of preimplantation embryos with genetically engineered retroviruses may also be used to introduce transgenes into an animal cell. For example, blastomeres have been used as targets for retroviral infection (Jaenisch, (1976) Proc. Natl. Acad. Sci USA 73:1260–1264). Transfection is typically achieved using a replication-defective retrovirus carrying the transgene (Jahner et al., (1985) Proc. Natl. Acad. Sci. USA 82:6927–6931; Van der Putten et al., (1985) Proc. Natl. Acad Sci USA 82:6148–6152). Transfection is obtained, for example, by culturing eight-cell embryos, from which the zona pellucida has been removed with fibroblasts which produce the virus (Van der Putten (1985), supra; Stewart et al., (1987) EMBO J. 6:383–388). The transfected embryos are then transferred to foster mothers for continued development. Alternatively, infection can be performed at a later stage. Virus or virus-producing cells can be injected into the blastocoele (Jahner et al., (1982) Nature 298:623–628). Yet another alternative method involves intrauterine retroviral infection of the midgestation embryos (Jahner et al. (1982), supra).

The advantages of retroviral infection methods include the ease of transfection and the insertion of a single copy of the transgene, which is flanked by the retroviral long terminal repeats (LTRs), into the chromosome. However, this method is not a preferred method because most of the founders will show mosaicism since infection occurs after cell division has begun. This necessitates outbreeding to establish homozygous and heterozygous lines suitable for analysis of gene expression. More importantly, the retroviral LTR sequences may interfere with the activity of the hINV upstream sequences in directing expression of the heterologous nucleic aid sequences.

iii. Embryonic Stem Cell Implantation

Another method of introducing transgenes into the germ line involves using embryonic stem (ES) cells as recipients of the expression vector. ES cells are pluripotent cells directly derived from the inner cell mass of blastocysts (Evans et al., (1981) Nature 292:154–156; Martin (1981) Proc. Natl. Acad Sci. USA 78:7634–7638; Magnuson et al., (1982) J. Embryo. Exp. Morph. 81:211–217; Doetchman et al., (1988) Dev. Biol. 127:224–227), from inner cell masses (Tokunaga et al., (1989) Jpn. J. Anim. Reprod. 35:113–178), from disaggregated morulae (Eistetter, (1989) Dev. Gro. Differ. 31:275–282) or from primordial germ cells (Matsui et al., (1992) Cell 70:841–847; Resnick et al., (1992) Nature 359:550–551). Expression vectors can be introduced into ES cells using any method which is suitable for gene transfer into cells, e.g., by transfection, cell fusion, electroporation, microinjection, DNA viruses, and RNA viruses (Johnson et al., (1989) Fetal Ther. 4 (Suppl. 1):28–39).

The advantages of using ES cells include their ability to form permanent cell lines in vitro, thus providing an unlimited source of genetic material. Additionally ES cells are the most pluripotent cultured animal cells known. For example, when ES cells are injected into an intact blastocyst cavity or under the zona pellucida, at the morula stage embryo, ES cells are capable of contributing to all somatic tissues including the germ line in the resulting chimeras.

Once the expression vector has been introduced into an ES cell, the modified ES cell is then introduced back into the embryonic environment for expression and subsequent transmission to progeny animals. The most commonly used method is the injection of several ES cells into the blastocoel cavity of intact blastocysts (Bradley et al., (1984) Nature 309:225–256). Alternatively, a clump of ES cells may be sandwiched between two eight-cell embryos (Bradley et al., (1987) in "Teratocarcinomas and Embryonic Stem Cells: A Practical Approach," Ed. Robertson E. J. (IRL, Oxford, U.K.), pp. 113–151; Nagy et al., (1990) Development 110:815–821). Both methods result in germ line transmission at high frequency.

Target cells which contain the heterologous nucleic acid sequences are recovered, and the presence of the heterologous nucleic acid sequence in the target cells as well as in the animal is accomplished as described supra.

4. Tissue Specific and Cell Type Specific Expression

Selective expression of the gene of interest in tissues and cells of transgenic animals may be determined using several methods known in the art as well as using methods described herein. For example, expression of mRNA encoded by the gene of interest may be determined by using in situ hybridization. This involves synthesis of an RNA probe which is specific for a portion of (or the entire) gene of interest, e.g. by using PCR. The PCR amplified fragment is subcloned into a plasmid (e.g., pbluescript (Stratagene)) and the RNA probe synthesized using labelled UTP (e.g. $^{35}$S-UTP) and RNA polymerase (e.g., T3 or T7 polymerase (Promega)). Paraffin-embedded tissue sections are mounted on slides, deparaffinized, rehydrated and the protein digested (e.g., with proteinase K), then dehydrated prior to hybridization with the RNA probe at the desired hybridization stringency. Slides are then developed for autoradiography using commercially available developers. Labelling of tissues and cells as detected on the autoradiographs indicates expression in those tissues and cells of the mRNA encoded by the gene of interest. Alternatively, mRNA encoded by the gene of interest may be detected by reverse transcription polymerase chain reaction (RT-PCR) as described herein (see, e.g., Example 3).

Alternatively, expression of the protein product of the gene of interest may be determined using immunohistochemical techniques. Briefly, paraffin-embedded tissue sections are dewaxed, rehydrated, treated with a first antibody which is specific for the polypeptide product of the gene of interest. Binding is visualized, for example, by using a secondary biotinylated antibody which is specific for the constant region of the primary antibody, together with immunoperoxidase and 3,3'-amiobenzidine as a substrate. Sections may then be stained with hematoxylin to visualize the cellular histology. Antibody binding of tissues and cells which is detected by antibody binding demonstrates expression of the protein product of the gene of interest in these tissues and cells.

Yet another alternative method for the detection of expression of the protein product of the gene of interest is by Western blot analysis wherein protein extracts from different tissues are blotted onto nitrocellulose filters, and the filters incubated with antibody against the protein product of the gene of interest, followed by detection of antibody binding using any of a number of available labels and detection techniques (see, e.g., Example 2).

C. Uses for the Transgenic Animals

The transgenic animals of this invention may be used to (a) screen compounds for anti-neoplastic activity, (b) screen compounds for carcinogenic and co-carcinogenic activity, (c) identify genes which play a role in neoplastic progression of epithelial cancers such as tracheal, easophageal, colon, epidermal, anal/rectal, lymph node, spleen, lung and cervical cancers, and (d) provide an in vivo model for epithelial cancers such as tracheal, easophageal, colon, epidermal, anal/rectal, lymph node, spleen, lung and cervical cancers.

In using the transgenic animals provided herein to screen potential anti-neoplastic compounds, it is anticipated that presently used compounds (e.g., the retinoids which have already been tested in clinical trials in patients with HPV disease) and anti-cancer compounds currently in use for chemotherapy of cancers of the trachea, esophagus, colon, epidermis, anus/rectum, lymph nodes, spleen and lung, in humans will be screened first because many of their effects on humans are already known. In this situation, the screening process can be used to gather data such as which compounds are most effective at particular stages of tracheal, easophageal, colon, epidermal, anal/rectal, lymph node, spleen, lung, and ectocervical cancer development. In addition, compounds which are derivatives of existing efficacious anti-cancer agents, or which have a new mechanism of action may also be administered singly or in combination to determine their effect in altering the incidence, rate of development, or pathology of epithelial cancers of the trachea, esophagus, colon, epidermis, anus/rectum, lymph nodes, spleen, lung, and ectocervix.

Another use of the transgenic mice of this invention is to screen potential carcinogens and co-carcinogens. One of skill in the art would appreciate that this may be achieved by exposing transgenic animals of this invention, which exhibit pre-neoplastic lesions (e.g., hyperplasias and dysplasias) to agents which are suspected of having carcinogenic or co-carcinogenic activity. These agents are administered either singly or in combination. Where a combination of agents is used, the agents may be administered simultaneously or sequentially.

An additional use of the trangenic animals provided herein is to determine the identity of genes which are involved in the cellular progression to pre-neoplastic and neoplastic states in epithelial tissues. This may be done, for example, by mating two different transgenic mice (e.g., a transgenic mouse which contains a gene or oncogene whose expression is under the control of a hINV promoter sequence, and another transgenic mouse containing HPV oncogenes that are regulated by a hINV promoter sequence) to produce a double transgenic animal. The double trangenic animal is then used to determine the frequency and rate of development of pre-neoplastic and neoplastic lesions. The identification of genes or oncogenes which accelerate malignant progression in tracheas, easophageal, colon, epidermal, anal/rectal, lymph node, spleen, lung, as well as ectocervical tissues, or which induce tumors in other than these tissues provides further targets for therapeutic treatment. Treatment may be accomplished, for example, by administeration to the animal of anti-sense nucleotide sequences which target the coding or non-coding regions of these genes and oncogenes, and/or of antibodies against the polypeptide products of the genes or oncogenes which are identified to play a role in malignant progression.

A further use of the herein provided transgenic animals is to develop an in vivo model for cervico-vaginal neoplastic progression. Human papillomaviurses are believed to be the etiologic agents for the majority of human cervical carcinoma. It is also believed that the HPV-16 E6 and E7 oncogenes, as well as sex hormones, play a significant role in the development of cervical cancer. The involvement of estrogen, estrogen-like compounds, and estrogen agonists and antagonists (e.g. tamoxifen and megestrerol) alone or in combination provides a model system in which to induce cervico-vaginal neoplastic progression. This model would then provide a system to screen candidate drugs (as described supra) (e.g., anti-estrogens and progestins) for their ability to circumvent cervico-vaginal neoplastic progression in this model.

One of skill in the art would appreciate that the above-described uses of the transgenic animals involve administration of potential anti-neoplastic compounds, carcinogens, or co-carcinogens alone or in combination, as well as the detection of the effect of such administration on cancer development and/or progression. Administration of potential anti-neoplastic compounds, carcinogens, co-carcinogens, and other compounds of interest is accomplished using any suitable route (e.g., oral, parenteral, rectal, controlled release transdermal patches and implants, etc.). Methods of parenteral delivery include topical, intra-arterial (e.g., directly to the tumor), intramuscular, subcutaneous, intramedullary, intrathecal, intraventricular, intravenous, intraperitoneal, or intranasal administration. Generally speaking the route of administration will depend on the stability of the compound, the susceptibility of the compound to "first pass" metabolism, the concentration needed to achieve a therapeutic effect, and the like. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

One of skill in the art would recognize that detection of the effect of the compound being tested on cancer may be determined according to standard techniques well-known in the art. These techniques include visual inspection, immunohistochemical techniques, and the like. For example, the change in the size of tumors may be monitored using calipers. The relative number and distribution of hyperplastic and dysplastic cells in relation to normal cells may be determined by histochemical analysis in combination with incorporation of 5-bromo-2'-deoxyuridine (BrdU) incorporation. Briefly, animals are injected intraperitoneally with 100 µg/g body weight of a 5 mg/ml solution of BrdU (Sigma) in a 10 mM Tris, 0.9% saline, 1 mM EDTA pH 8.0 buffer. After 2 hours the animals are sacrificed, and tissues are fixed, processed, embedded in paraffin, and 5 µm sections obtained. After deparaffinization and rehydration, the slides are immersed in 2N HCl for 1 hr, extensively rinsed in tap water, and equilibrated in PBS. The sections are then treated for 60 sec. with 0.1% bacterial protease type XXIV (Sigma), rinsed extensively in tap water, equilibrated in PBS, and blocked in 3% normal goat serum. A 1:50 dilution of a biotinylated mouse monoclonal anti-BrdU antibody (Br-3) (CalTag) is applied, and the sections incubated overnight at 4° C. Antibody binding is detected using a peroxidase/avidin/biotin complex (ABC) (Vector Laboratories) with 3,3'-diaminobenzidine (Sigma) as the chromogen. Dividing cells (i.e., which incorporate BrdU) are then visualized using microscopy.

Following initial screening, a compound that appears promising is further evaluated by administering various concentrations of the compound to the transgenic animals provided herein in order to determine an approximate therapeutic dosing range.

Animal testing may be supplemented and confirmed by testing on human subjects. However, the animal models herein provided allow the testing of a large number of compounds, both by the methods described above and other methods known in the art, in a system similar in many important respects to that in humans.

EXPERIMENTAL

The following examples serve to illustrate certain preferred embodiments and aspects of the present invention and are not to be construed as limiting the scope thereof.

In the experimental disclosure, which follows, the following abbreviations apply: bp (base pair); kb (kilobases); kd (kilodaltons); p (plasmid); Boehringer Mannheim (Indianapolis, Ind.); CalTag (Burlingame, Calif.); Promega (Madison, Wis.); Sigma (St. Louis, Mo.); Stratagene (San Diego, Calif.); Vector Laboratories (Burlingame, Calif.).

EXAMPLE 1

Generation of Transgenic Mice

A. Construction of hINV transgenes.

Figure 3:
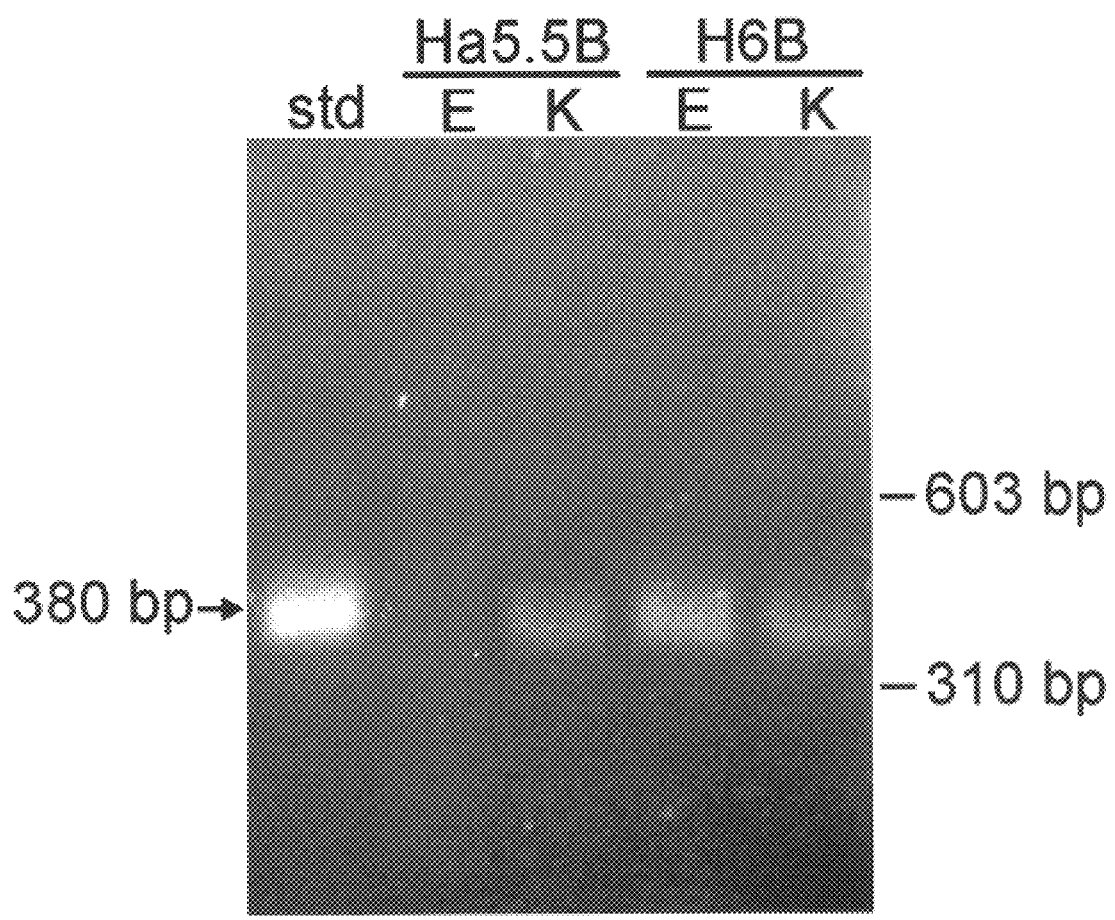
FIG. 3 shows by agarose gel and ethidium bromide staining the detection of hINV mRNA synthesis in tissues.

E13E was constructed by EcoR1 digestion of λ phage, Charon 4A λI-3 (Eckert and Green "Structure and evolution of the human involucrin gene" Cell 46:583–589, 1986). A 13-kb EcoR1 fragment was then subcloned into pBKS (+) to yield pBKS-E13E. The EcoR1 insert from this plasmid is shown in FIG. 3. The H6B transgene is a 6-kb HindIII/BamHI fragment that was derived by restricting Charon 4A λI-3 with HindIII/BamHI and subcloning the resulting 6-kb fragment into HindIII/BamHI-restricted pSP64 to yield pS64λI-3 H6B (Eckert and Green "Structure and evolution of the human involucrin gene" Cell 46:583–589, 1986). Promoter deleted transgenes were constructed by taking advantage of unique restriction sites located upstream of the transcription start site. Consequently, the Ha5.5B transgene was generated by digesting pSP64λI-3 H6B with HaeII/BamHI and isolating the HaeIIBamHI. Likewise, the A4.3B and K4B transgenes were isolated from pSP64λI-3 H6B by digesting with AccI/BamHI and KpnI/BamHI, respectively. P3.4B was generated by complete BamHI and partial PstI segment immediately upstream of the basal promoter in P3.4B using a polylinker. Maps of the transgenes are shown in FIGS. 3 and 9. Multiple E13E (one), A4.3N (one), K4B (one), H6B (four), Ha5.5B (three), P3.4B (five) and DRR-P3.4B (three) transgenic lines were characterized.

To construct H6B(AP1-5 mm), plasmid pINV-2473 (AP1-5 mm/Sp1), which contains the AP1-5 mutant site (Welter, et al. "Fos-related antigen (Fra-1), junB, and junD activate human involucrin promoter transcription by binding to proximal and distal AP1 sites to mediate phorbol ester effects on promoter activity" J. Biol. Chem. 270:12614–12622, 1995; Banks, et al., "Characterization of human involucrin promoter distal regulatory region transcriptional activator elements-a role for Sp1 and AP1 binding sites" Biochem. J. 331:507–512, 1999), was digested with HindIII/KpnI. This fragment was used to replace the corresponding native sequence in pSP64λI-3 H6B to create H6B(AP1-5 mm). The DRR-P3.4B(AP1-5 mm) transgene was constructed by HindIII/Bg/II digestion of H6B(AP1-5 mm) and subsequent subcloning of the Hind III/Bg/II fragment containing the AP1-5 mutation into HindIII/Bg/II-digested DRR-P3.4B to create DRR-P3.4B(AP1-5 mm). For microinjection, the transgenes were released from plasmid sequences by restriction with HindlIII/Bam/HI.

The hINV transgenes are shown in FIG. 1. E12E includes approximately 5,000 bp of upstream sequence, the transcribed hINV gene, and 4.5 kb of downstream sequence. All other constructs are truncated at a BamHI site located just downstream of the transcription stop sequence. H6B, Ha5.5B, A4.3B and K4B are progressively truncated from the 5' end and contain 2473, 1953, 1333 and 986 bp of upstream regulatory region, respectively.

B. Generation of trangenic mice.

Mouse embryos from a B6CBAxB6CBA mating were injected with each hINV gene construct and implanted into surrogate mothers using standard methodology (Hogan, et al., *Manipulating the mouse embryo, a laboratory manual*, Cold Spring Harbor Laboratory, NY, 1988). The offspring were characterized for the presence of the human involucrin (hINV) transgene by blotting of tail DNA (Crish, et al., "Tissue-specific and differentiation-appropriate expression of the human involucrin gene in transgenic mice: an abnormal epidermal phenotype " *Differentiation* 53:191–200, 1993; Hogan, et al, *Manipulating the mouse embryo, a laboratory manual*, Cold Spring Harbor Laboratory, NY, 1988).

EXAMPLE 2

A 520-bp Segment of the hINV Upstream Regulatory Region is Required for hINV Expression in Epidermis.

A. Detection of hINV protein expression.

To detect expression of the hINV protein in mice, expression of the hINV protein by immunoblot of whole cell extracts was assayed in epidermis and kidney as described proviously (Crish, et al., "Tissue-specific and differentiation-appropriate expression of the human involucrin gene in transgenic mice: an abnormal epidermal phenotype" *Differentiation* 53:191–200, 1993). Briefly, to detect hINV expression in mouse tissues, total protein extracts were prepared from tissue samples in Laemmli sample buffer, electrophoresed on acrylamide gels, and transferred to nitrocellulose for immunoblot. The blot was incubated with a primary antibody prepared against human involucrin, diluted 1:8000 as described previously (Crish, et al., "Tissue-specific and differentiation-appropriate expression of the human involucrin gene in transgenic mice: an abnormal epidermal phenotype " *Differentiation* 53:191–200, 1993), followed by visualization using a chemiluminescent detection system. To detect hINV in tissue sections, samples were fixed in buffered formalin, embedded in paraffin, and sectioned (Crish, et al., "Tissue-specific and differentiation-appropriate expression of the human involucrin gene in transgenic mice: an abnormal epidermal phenotype" *Differentiation* 53:191–200, 1993). The sections were deparaffinized, blocked, incubated with primary anti-hINV antibody and secondary detection agents exactly as described previously (Crish, et al., "Tissue-specific and differentiation-appropriate expression of the human involucrin gene in transgenic mice: an abnormal epidermal phenotype" *Differentiation* 53:191–200, 1993). The involucrin antibody was used at a dilution of 1:1000 and was preabsorbed on 3T3 fibroblast cells prior to use. Equivalent quantities of protein extract (15 $\mu$g) were immunoblotted. As shown in FIG. 2A, hINV protein is detected in epidermis in E13E and H6B mice, but not in Ha5.5B, A4.3B or K4B mice. In contrast to the differences in hINV expression in epidermis, hINV transgene expression is retained in the kidney of all tansgenic lines (FIG. 2B). These results indicate that the 520-bp DNA segment located from −2473 to −1953 is required for expression of the hINV transgene in epidermis. Nontransgenic mice did not produce hINV.

B. Detection of hINV mRNA.

The above experiments show that hINV protein was present in the epidermis and kidney of E13E and H6B mice. However, these results do not demonstrate that hINV is synthesized in these tissues. To directly demonstrate synthesis, we assayed for hINV mRNA by RT-PCR. Expression of hINV mRNA in mouse tissues was detected by reverse transcription polymerase chain reaction (RT-PCR). Two micrograms of total RNA, isolated from mouse tissue, was reverse transcribed in 10 mM Tris-HCL buffer (pH 8.3) containing 50 mM KCL, 5 mM $MgCl_2$, 1 mM of each dNTP, 1.6 $\mu$g of oligo-p(dt)$_{15}$ primer, 50 units of RNase inhibitor and 20 units of reverse transcriptase (Boehringer Mannheim) for 10 min at 25° C. and for 60 min at 42° C. in a 20 $\mu$l reaction. The reverse transcription was inactivated by heating and 20 $\mu$l of the reverse transcription reaction was added to a 100 $\mu$l PCR amplification reaction containing 10 mM Tris-HCL, Ph 8.3, 50 mM KCL, 1.5 mM $MgCl_2$, 1.5 mM each dNTP, 0.2 $\mu$M each upstream (5'-CTC CAC CAA AGC CTC TGC (SEQ ID NO:2), in exon 1) and downstream (5'-CTG CTT AAG CTG CTG CTC (SEQ ID NO:3), in exon 2) primers and 2.5 units of Taq DNA polymerase. The PCR cycling reactions were 96° C. for 1 min, 57° C. for 1 min and 72° C. for 2 min for 35 cycles. These primers amplify a 380 bp segment of the hINV mRNA sequence. Because the primers are in different exons, PCR amplification of contaminating genomic DNA can be distinguished by production of a much larger band. β-actin was amplified in parallel reactions as a control. FIG. 3 shows that mRNA encoding hINV is produced in the epidermis (E) and kidney (K) of H6B mice, but not in the epidermis of Ha5.5B mice. Thus, hINV is synthesized in these tissues and loss of hINV expression in the Ha5.5B as compared with H6B is associated with loss of hINV mRNA.

EXAMPLE 3

Differentiation Appropriate Expression of the hINV Transgene

We used immunological techniques to evaluate the differentiation-dependence of expression (FIG. 4). hINV was detected in the upper spinous and granular layers in footpad epidermis (EP1, left hand column) in E13E and H6B mice but no expression was detected in the basal layer (arrowheads). Suprabasal expression was also observed in the ectocervical epithelium (EC, right hand column) in these mice. In contrast, no expression was observed in epithelium or epidermis of transgenic strains Ha5.5B or K4B (FIG. 4), and no expression was observed in nontransgenic mice (not shown). FIG. 5 shows transgenic expression in the kidney of K4B mice. In this, and all other lines, expression in kidney was confined to the epithelia lining the distal convoluted tubule in transgenic lines.

The results discussed in Examples 3 and 4 suggest the regulatory elements are localized within the −2473/−1953 segment. To identify the sequence of these regulatory elements, the entire 2473-bp hINV upstream regulatory region (−2473/−7) was sequenced. The upstream regulatory region from the hINV gene (Eckert and Green "Structure and evolution of the human involucrin gene" *Cell* 46:583–589, 1986) was isolated and sequenced using Maxam-Gilbert (Echert "New vectors for rapid sequencing of DNA fragments by chemical degradation" *Gene (Amst.)* 51:247–254, 1987) and dideoxy sequencing (Sanger, et al. "DNA sequencing with chain-terminating inhibitors" *Proc Natl Acad Sci, USA* 74:5463–5467, 1977). The complete sequence was determined in both directions. The results are shown in FIG. 6. These results suggest that the DRR of SEQ ID NO:1 supports the expression of hINV in suprabasal epithelial cells.

EXAMPLE 4

The Distal Regulatory Region is Sufficient to Drive Transcription in Epidermis

Figure 2:
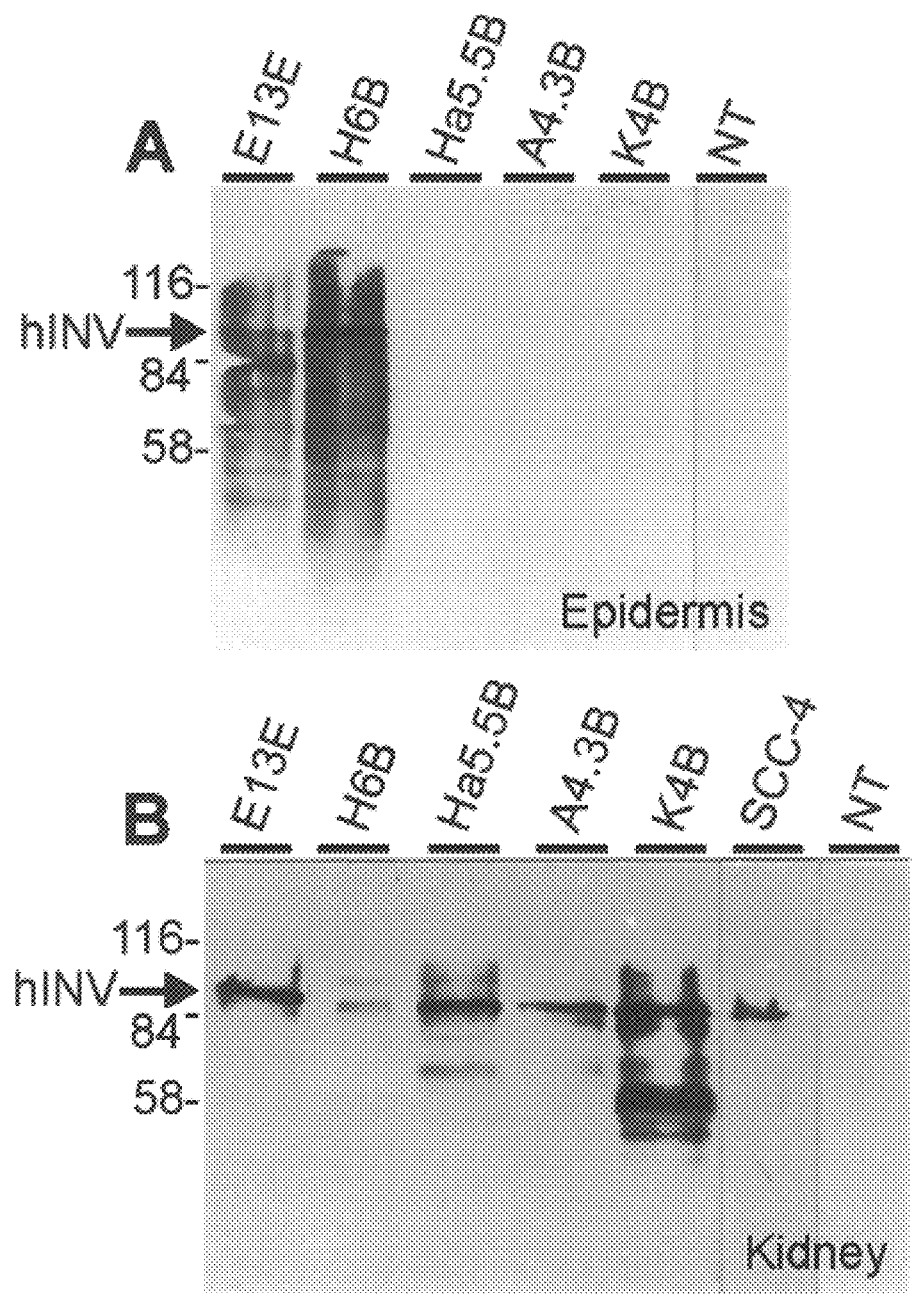
FIG. 2 shows by Western blot the detection of hINV in epidermis (2A) and kidney (2B) (NT=not treated).
Figure 4:
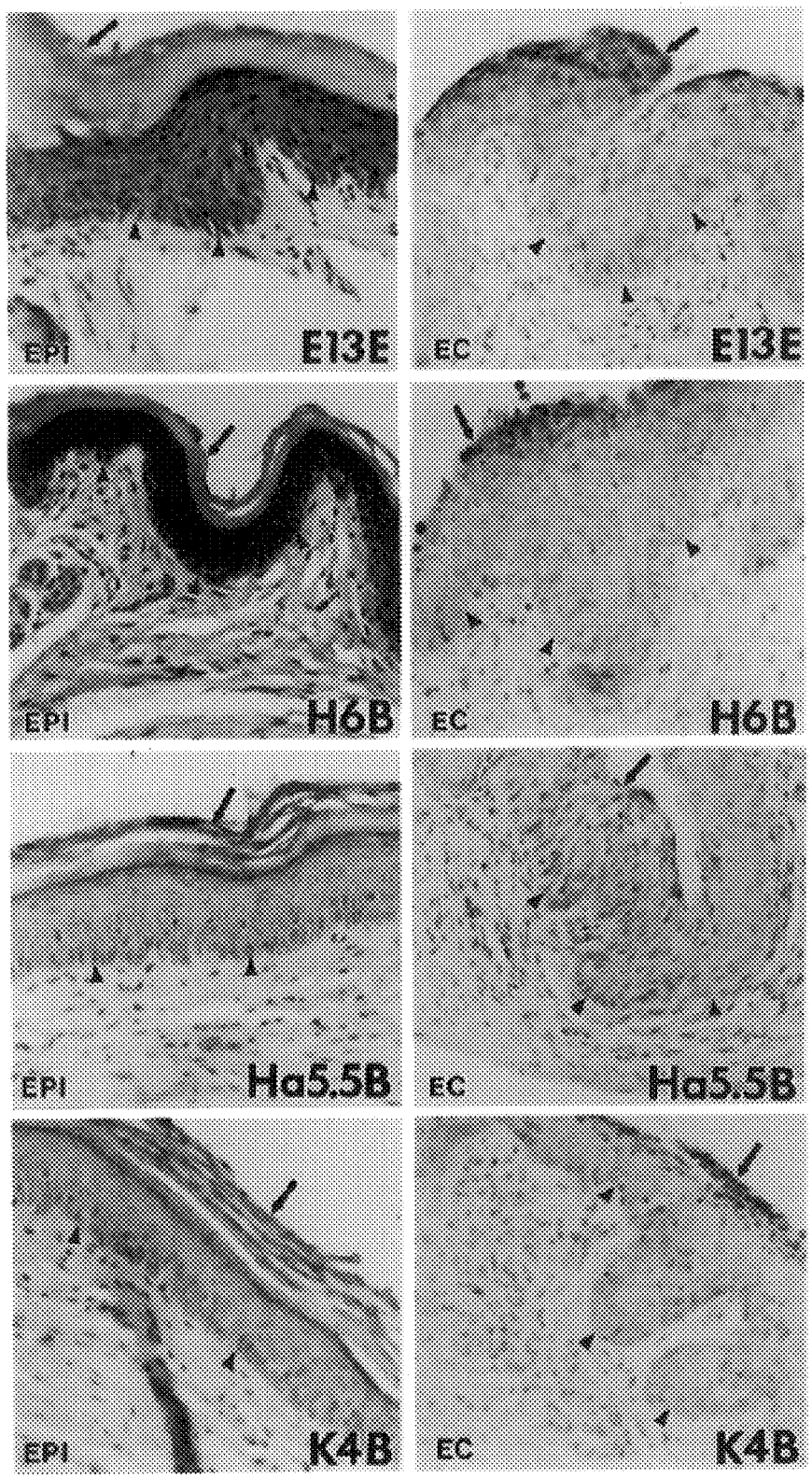
FIG. 4 is a color image showing the immunodetection (primary antibody followed by horseradish peroxidase linked secondary antibody) of hINV in epidermis (EP1) and ectocervix (EC).
Figure 5:
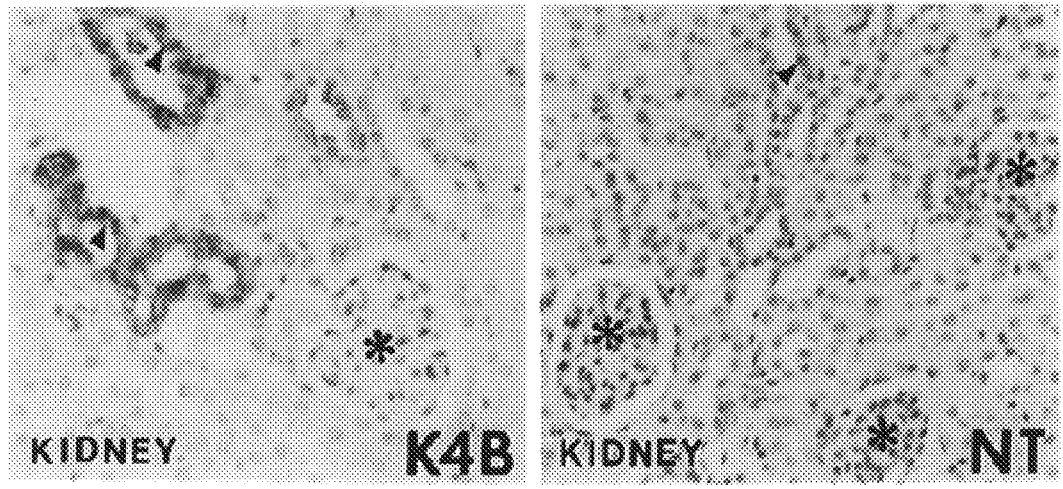
FIG. 5 is a color image showing the immunodetection (primary antibody followed by horseradish peroxidase linked secondary antibody) of hINV in kidney.
Figure 7A:
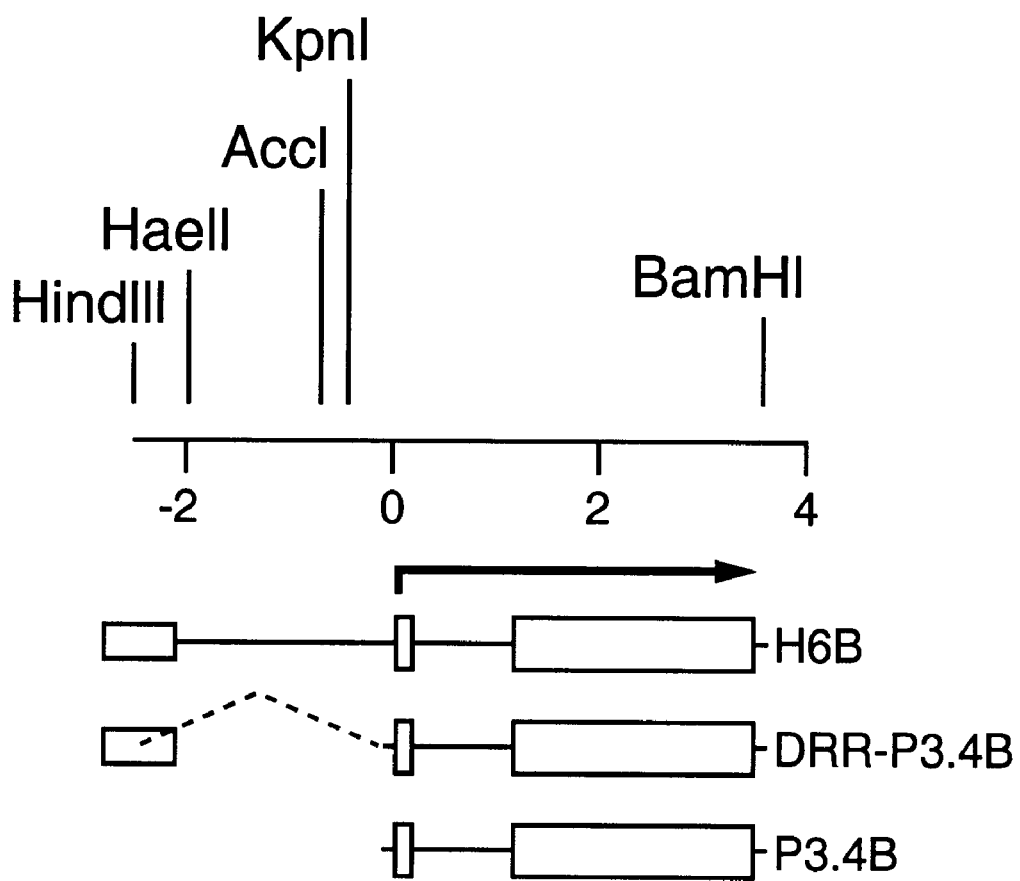
FIG. 7A shows the structure of constructs P3.4B, DRR-P3.4B and H6B.
Figure 7B:
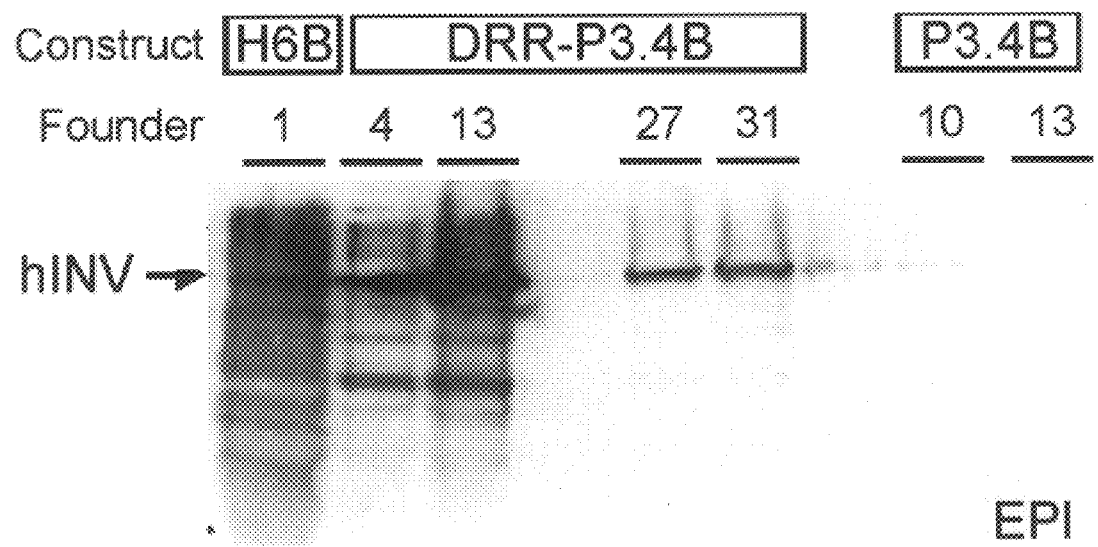
FIG. 7B shows by Western blot that the distal regulatory region (DRR) region is necessary for expression in epidermis.
Figure 8:
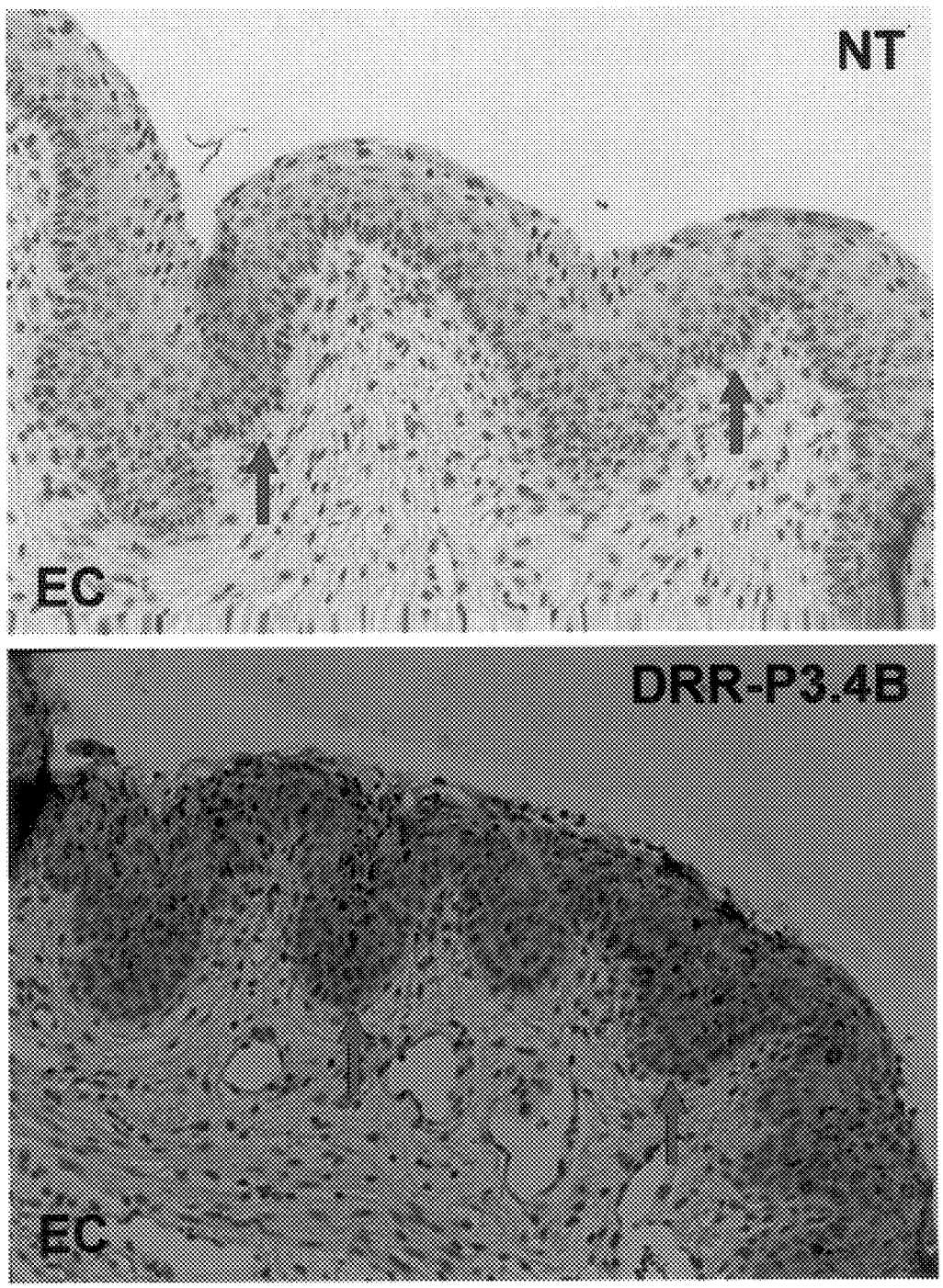
FIG. 8 is a color image showing the imunodetection of DRR-P3.4B expression.

The results of experiments shown in FIGS. 2, 3 and 4 suggest that the sequence from −2473 to −1953 of SEQ ID NO:1 is required for expression in stratifying epithelia. The basal hINV promoter construct, P3.4B, which contains only 41 bp of the upstream sequence from the start codon (bases from −41 to −7 of SEQ ID NO:1) (FIG. 7A), shows no expression in epidermis (FIG. 7B). Fusion of the DRR segment (−2473/−1953) immediately upstream of the basal promoter restores expression in stratifying epithelia of epidermis (FIG. 7B). The DRR-P3.4B construct is expressed at a level compared with that observed with H6B (FIG. 7B). Immunohistological examination of the pattern of expression reveals that the DRR-P3.4B drives expression in the suprabasal layers in the ectocervical epithelium (FIG. 8). These results suggest that the DRR region (from nucleotides −2473 to −1953 of FIG. 6), in combination with the basal promotor region (from nucleotides −41 to −7 of FIG. 6) supports expression of the hINV gene in suprabasal layers in the ectocervical epithelium as well as the intact sequence of FIG. 6 (SEQ ID NO:1).

EXAMPLE 5

AP1-S is Required for Optimal hINV Expression in Epidermis.

Figures 9A, 9B:
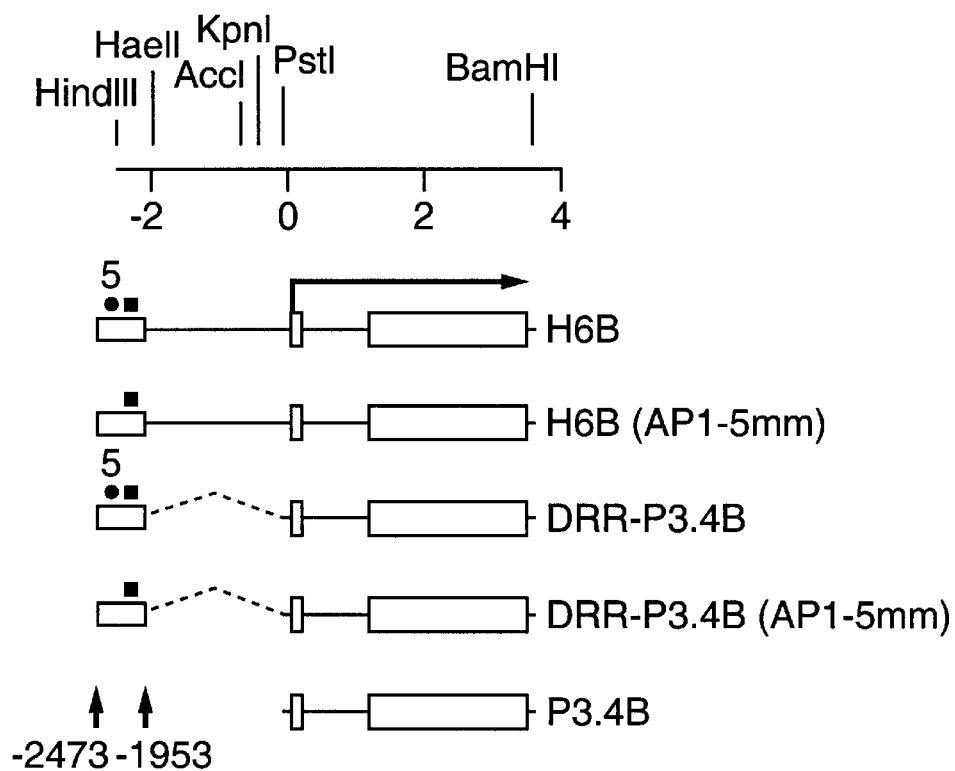
FIG. 9A shows the structure of hINV transgenes used in Examples 7, 8 and 9. The open box depicts the hINV promoter distal regulatory region (DRR, −2473/−1953). The arrows encompasses the transcribed region including the shaded small and large rectangles denoting, respectively, the first and second exons. The shaded circle and box over the DRR indicate, respectively, the AP1-5 and Sp1 sites. Distances in kilobases are indicated as positive downstream and negative upstream of the transcription start site.
FIG. 9B shows the sequence of the HINV promoter AP1-5 site (5'-TGAGTCAG-3' from nucleotides −2122 to −2115, FIG. 6: SEQ ID NO:4) and Sp1 site 5'-GGGCGGG-3' from nucleotides −2113 to −2108.

It was hypothesized that the AP1-5 site located in the hINV DRR (distal regulatory region) is required for tissue and cell specific involucrin expression in epidermis. To test this hypothesis, we generated transgenes lacking a functional AP1-5 site (FIG. 9A). Construct H6B includes the full-length (2473 nucleotide) promoter (Crish, et al., "Tissue-specific and differentiation-appropriate expression of the human involucrin gene in transgenic mice: an abnormal epidermal phenotype" *Differentiation* 53:191–200, 1993). P3.4B, in contrast, includes only the 41 nucleotides of promoter region immediately upstream of the transcription start site. In DRR-P3.4B, the 520 bp distal regulatory region, shown as an open box, is cloned adjacent to the basal promoter. Parallel constructs lacking a functional AP1-5 site, H6B(AP1-5 mm) and DRR-P3.4B(AP1-5 mm), were constructed encoding the mutant sequence underlined in FIG. 9B. In these studies we use human involucrin as our reporter gene. This is possible because the antibody used detects human but not mouse involucrin (LaCelle, et al. "In vitro cross-linking of recombinant human involucrin" *Pharmacol Appl Skin Physiol* 11:214–226, 1998). This approach avoids problems associated with differences in turnover rate of involucrin as compared to other possible reporter proteins, such as β-galactosidase or luciferase, in tissues.

Figure 10:
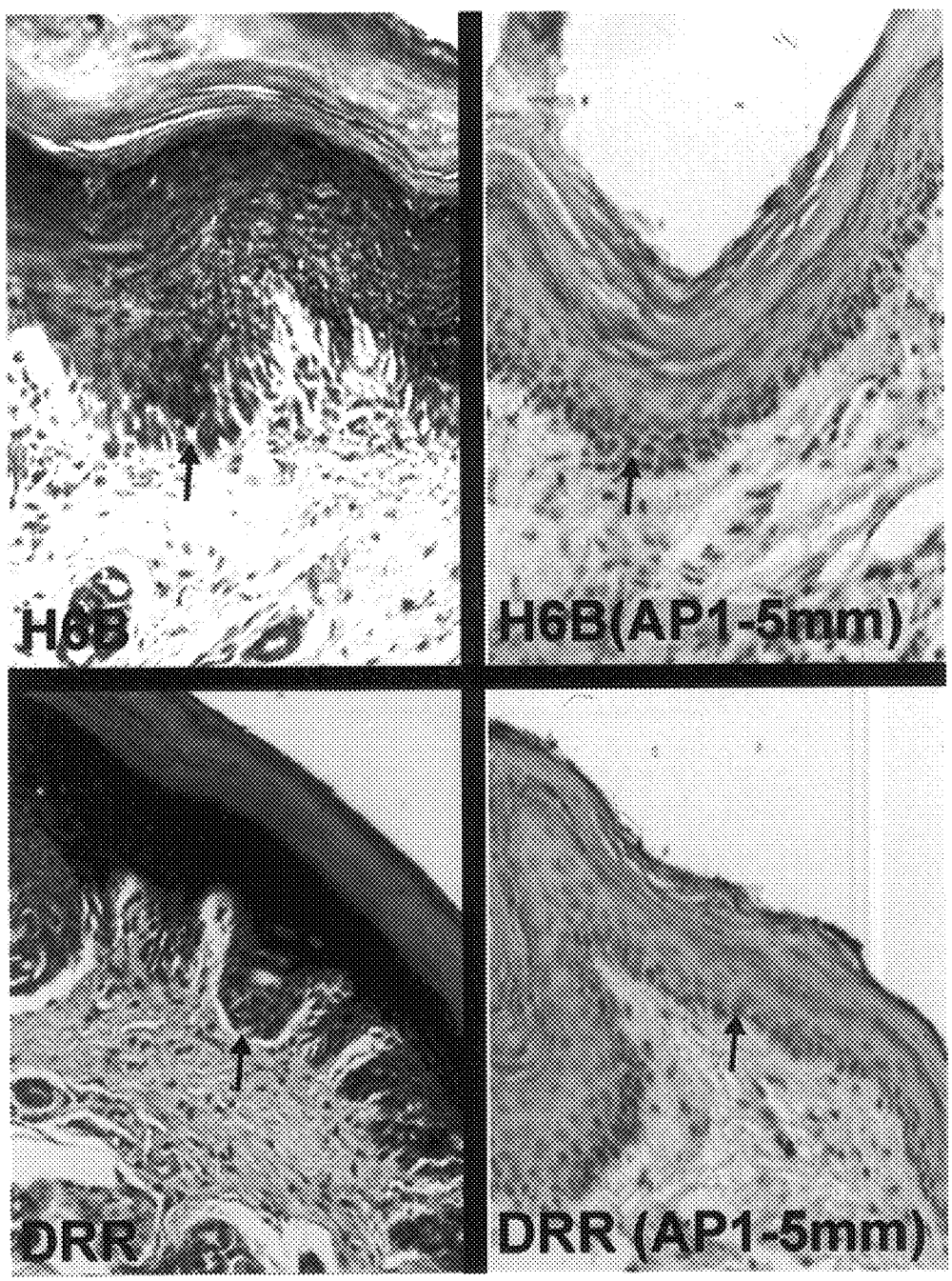
FIG. 10 is a color image showing the effect of AP1-5 mutation on hINV expression in foot pad.

We began by examining the ability of the constructs shown in FIG. 9 to drive expression in footpad epidermis. Footpad is a useful tissue for study because the multiple layers make it easy to visualize differentiation-dependent expression. As shown in FIG. 10, H6B directs expression to the suprabasal (spinous and granular) layers. DRR-P3.4B produces an essentially identical pattern of suprabasal expression. Remarkably, mutation of the AP1-5 site, in the context of the full-length promoter, results in a loss of footpad expression, H6B(AP1-5 mm). Moreover, expression is also lost when AP1-5 is mutated in the context of the isolated DRR, DRR-P3.4B(AP1-5 mm). Thus, mutation of AP1-5, either in the context of the full length promoter or in the isolated DRR, markedly reduces hINV expression in footpad epidermis.

EXAMPLE 6

AP1-5 is required for expression in esophagus and cervix.

In addition to epidermis, involucrin is expressed in other stratifying surface epithelia (Rice and Green "Presence in human epidermal cells of a soluble protein precursor of the cross-linked envelope: activation of the cross-linking by calcium ions" *Cell* 18:681–694, 1979; Murphy, et al. "Involucrin expression in normal and neoplastic human skin: a marker for keratinocyte differentiation" *J Invest Dermatol* 82:453–457, 1984; Banks-Schlegel, et al. "Involucrin synthesis and tissue assembly by keratinocytes in natural and cultured human epithelia" *J Cell Biol* 90:732–737, 1981). To determine whether AP1-5 is required for hINV expression in these tissues, we measured hINV levels in esophagus and cervix. As shown in FIG. 11, H6B and DRR drive suprabasal expression in esophagus and cervix. In contrast, mutation of the AP1-5 site, in either the DRR or full-length promoter contexts, reduces hINV expression in both cervix and esophagus.

EXAMPLE 7

Mutation of AP1-5 results in reduced hINV protein levels.

To confirm the immunohistological data and compare the level of hINV expression between mutant and intact constructs, we prepared tissue extracts from footpad epidermis, back epidermis, and esophagus, and measured hINV levels by immunoblot. As displayed in FIG. 12, H6B and DRR-P3.4B, which contain the intact AP1-5 site (+), produce high level hINV expression in each of these surface epithelia. In contrast, markedly reduced expression is observed in mice harboring the AP1-5 site mutant constructs (−). Although the level of expression is markedly reduced in these mice, protein expression by the gene is not turned completely off. This is in contrast to the complete lack of expression in mice containing construct P3.4B, the basal promoter construct (not shown) (Crish, et al., "Tissue-specific and differentiation-appropriate expression of the human involucrin gene in transgenic mice: an abnormal epidermal phenotype" *Differentiation* 53:191–200, 1993).

Figure 12:
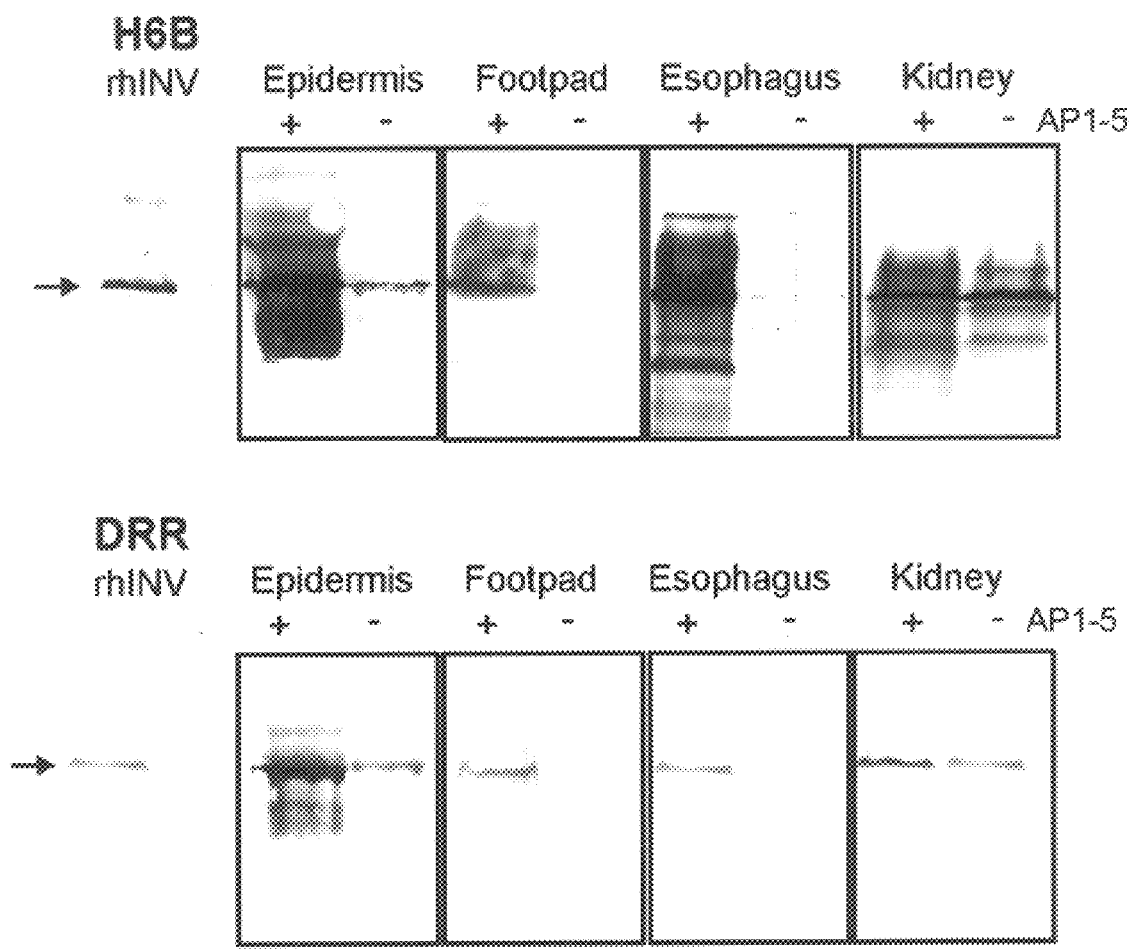
FIG. 12 shows the detection of hINV protein by Western blot in back epidermis, footpad epidermis, esophageal epithelium and kidney. The arrows indicate hINV migration. The lane marked rhINV contains recombinant human involucrin electrophoresed as a standard.

In previous reports, we described hINV transgene expression in the epithelia lining the proximal convoluted tubules of the kidney (Crish, et al., "Tissue-specific and differentiation-appropriate expression of the human involucrin gene in transgenic mice: an abnormal epidermal phenotype" *Differentiation* 53:191–200, 1993). This expression serves as a marker for integrity of the transgene, as transgene-dependent expression is observed in kidney independent of surface epithelial cell expression. As shown in FIG. 12, kidney expression is observed for all of the constructs, whether the AP1-5 site is intact or mutated. That the level of expression is maintained in the kidney argues that the reduced expression in the epithelia of AP1-5 mm mice is not due to inappropriate integration and/or rearrangement of the transgene.

These results support the conclusion that the AP1-5 site is specifically involved in regulating the level of hINV expression in surface epithelia, and also suggests a role in guiding tissue-specific expression. Table 2 summarizes the immunohistological results from individual mouse strains. This summary emphasizes the remarkably consistent results that are observed in that in each case where the AP1-5 site is mutated (AP1-5 mm), epithelial expression, as detected by immunohistological methods, is reduced to undetectable levels.

TABLE 2

Immunohistological detection of hINV transgene expression.

| Transgene (strain) | Epidermis | Footpad | Cervix | Esophagus | Kidney |
|---|---|---|---|---|---|
| H6B (1) | S | S | S | S | PCT |
| H6B (2) | S | S | S | S | PCT |
| H6B AP1-5mm (10) | — | — | — | — | PCT |
| H6B AP1-5mm (11) | — | — | — | — | PCT |
| H6B AP1-5mm (15) | — | — | — | — | PCT |
| DRR (4) | S | S | S | S | PCT |
| DRR (31) | S | S | S | S | PCT |
| DRR AP1-5mm (25) | — | — | — | — | PCT |

Expression was detected using an human involucrin-specific antibody prepared against recombinant human involucrin (LaCelle, et al., *Pharmacol Appl Skin Physiol* 11:214–226, 1998). S indicates normal suprabasal expression, PCT indicates expression in the kidney proximal convoluted tubule (Crish, et al., *Differentiation* 53:191–200, 1993; Crish, et al., *J Cell Biol*, 273:30460–30465, 1998),—indicates absence of expression.

It should be clear from the foregoing that the present invention provides materials and methods for the generation of transgeneic animals encoding genes under the regulation of portions of the nucleotide sequence of FIG. 6 (SEQ IN NO:1). Furthermore, it should be clear for the foregoing that the present invention provides materials and methods for the screening of therapeutics for eptithelial neoplasia.

What is claimed is:

1. A purified oligonucleotide comprising the nucleotide sequence from nucleotide 1 to nucleotide 521 of SEQ ID NO:1.

2. The oligonucleotide of claim 1, wherein said oligonucleotide additionally comprises the operably linked nucleotide sequence from nucleotide 2434 to nucleotide 2467 of SEQ ID NO:1.

3. The oligonucleotide of claim 1 or 2, wherein said nucleotide sequence is operably linked to a nucleic acid sequence of interest.

4. A recombinant expression vector comprising the nucleotide sequence from nucleotide 1 to nucleotide 521 of SEQ ID NO:1.

5. The recombinant expression vector of claim 4, wherein said nucleotide sequence is operably linked to a nucleic acid sequence of interest.

6. A recombinant expression vector comprising the nucleotide sequence from nucleotide 1 to nucleotide 521 of SEQ ID NO:1 operably linked to the sequence from nucleotide 2434 to nucleotide 2467 of SEQ ID NO:1.

7. The recombinant expression vector of claim 6, wherein said nucleotide sequence is operably linked to a nucleic acid sequence of interest.

8. An isolated host cell comprising a recombinant expression vector wherein said recombinant expression vector comprises the nucleotide sequence from nucleotide 1 to nucleotide 521 of SEQ ID NO:1.

9. A mouse cell comprising a recombinant expression vector wherein said recombinant vector comprises the nucleotide sequence from nucleotide 1 to nucleotide 521 of SEQ ID NO:1.

10. The mouse cell of claim 9, wherein said mouse cell is a fertilized egg cell.

11. The mouse cell of claim 9, wherein said mouse cell is in a blastomere.

12. The mouse cell of claim 9, wherein said mouse cell is in an eight-cell embryo.

13. The mouse cell of claim 9, wherein said mouse cell is in a midgestation embryo.

14. The mouse cell of claim 9, wherein said mouse cell is an embryonic stem cell.

15. A transgenic mouse displaying tissue specific expression of a nucleic acid sequence of interest, wherein said transgenic mouse comprises the nucleotide sequence from nucleotide 1 to nucleotide 521 of SEQ ID NO:1.

16. The transgenic mouse of claim 15, wherein said tissue is selected from the group consisting of uroepithelial tissue and stratified squamous epithelial tissue.

17. The transgenic mouse of claim 16, wherein said stratified squamous epithelial tissue is in an organ selected from the group consisting of epidermis, esophagus and cervix.

18. The transgenic mouse of claim 17, wherein said tissue specific expression is cell type specific.

19. The transgenic mouse of claim 18, wherein said cell in said stratified squamous epithelial tissue is suprabasal.

20. The transgenic mouse of claim 15, wherein said nucleic acid sequence of interest is a coding sequence of an oncogene.

21. The transgenic mouse of claim 20, wherein said oncogene is a human papillomavirus 16 oncogene.

22. A method for selective expression of a nucleic acid sequence of interest in epithelial cells of a mouse, comprising:
   a) providing:
      i) a transgene, wherein said transgene contains the nucleotide sequence from nucleotide 1 to nucleotide 521 of SEQ ID NO:1 operably linked to said nucleic acid sequence of interest;
      ii) an embryonic stem cell of a mouse; and
      iii) a pseudopregnant mouse; and
   b) introducing:
      said transgene into said embryonic stem cell to produce a transgenic embryonic stem cell; and
   c) introducing:
      said transgenic embryonic stem cell into said pseudopregnant mouse under conditions such that said pseudopregnant mouse delivers progeny of said transgenic embryonic stem cell, wherein said nucleic acid sequence of interest is selectively expressed in said epithelial cells of said progeny.

23. The method of claim 22, further comprising d) identifying at least one offspring of said progeny wherein said nucleic acid sequence of interest is selectively expressed in said epithelial cells of said offspring.

24. The method of claim 22, wherein said transgene further comprises the nucleotide sequence from nucleotide 2434 to nucleotide 2467 of SEQ ID NO:1.

25. A method for producing a transgenic mouse, comprising:
   a) providing:
      i) a transgene, wherein said transgene contains the nucleotide sequence from nucleotide 1 to nucleotide 521 of SEQ ID NO:1 operably linked to one or more oncogenes;
      ii) an embryonic stem cell of a mouse; and
      iii) a pseudopregnant mouse;
   b) introducing:
      said transgene into said embryonic stem cell to produce a transgenic embryonic stem cell; and
   c) introducing:
      said transgenic embryonic stem cell in to said pseudopregnant mouse under conditions such that said pseudopregnant mouse delivers progeny of said transgenic embryonic stem cell; and
   d) identifying at least one offspring of said progeny, wherein
      said oncogene is selectively expressed in epithelial cells of said offspring.

26. The method of claim 25, wherein said epithelial cell is suprabasal.

27. The method of claim 25, wherein said oncogene is selected from human papillomavirus 16 oncogne E6 nucleic acid sequence and human papilloma virus 16 oncogne E7 nucleic acid sequence.

28. A method of screening anti-neoplastic compounds, comprising:
   a.) providing:
      i) the transgenic mouse of claim 19 or 20; and
      ii) a compound suspected of having anti-neoplastic activity;
   b) administering said compound to said transgenic mouse to produce a treated transgenic mouse; and
   c) detecting anti-neoplastic activity in said treated transgenic mouse, thereby identifying said compound as anti-neoplastic.

* * * * *